(12) United States Patent
Koshimizu et al.

(10) Patent No.: US 8,293,529 B2
(45) Date of Patent: Oct. 23, 2012

(54) METHOD FOR INDUCING DIFFERENTIATION OF PLURIPOTENT STEM CELLS INTO CARDIOMYOCYTES

(75) Inventors: Uichi Koshimizu, Osaka (JP); Tomofumi Tanaka, Ibaraki (JP); Kayoko Kawashima, Takatsuki (JP); Michinori Kadokura, Nagaokakyo (JP)

(73) Assignee: Daiichi Sankyo Company, Limited, Chuo-ku, Tokyo (JP)

( * ) Notice: Subject to any disclaimer, the term of this patent is extended or adjusted under 35 U.S.C. 154(b) by 778 days.

(21) Appl. No.: 12/298,565

(22) PCT Filed: Apr. 27, 2007

(86) PCT No.: PCT/JP2007/059242
§ 371 (c)(1), (2), (4) Date: Oct. 27, 2008

(87) PCT Pub. No.: WO2007/126077
PCT Pub. Date: Nov. 8, 2007

(65) Prior Publication Data
US 2009/0325288 A1 Dec. 31, 2009

(30) Foreign Application Priority Data

Apr. 28, 2006 (JP) ................................. 2006-125148
Jan. 30, 2007 (JP) ................................. 2007-019531

(51) Int. Cl.
*C12N 5/00* (2006.01)
(52) U.S. Cl. ......................... 435/366; 435/352; 435/363
(58) Field of Classification Search ........................ None
See application file for complete search history.

(56) References Cited

U.S. PATENT DOCUMENTS

| | | | |
|---|---|---|---|
| 5,843,780 | A | 12/1998 | Thomson |
| 6,015,671 | A | 1/2000 | Field |
| 6,090,622 | A | 7/2000 | Gearhart et al. |
| 2004/0014209 | A1 | 1/2004 | Lassar et al. |

FOREIGN PATENT DOCUMENTS

| | | | |
|---|---|---|---|
| EP | 1674562 | * | 6/2006 |
| JP | 2005/224155 | | 8/2005 |
| WO | 03/006950 | | 1/2003 |
| WO | 2005/033298 | | 4/2005 |
| WO | 2005/118782 | | 12/2005 |

OTHER PUBLICATIONS

Naito et al., 28th Annual Meeting of the Molecular Biology Soc. of Japan, 2005, Hakata, Japan.*
Runke, Stem Cells 24:428-436, 2003.*
Keller, Genes and Development, 19:1129-1155, 2005.*
Wang et al., BBRC, 330:934-942, 2005.*
European Search Report mailed Nov. 3, 2009 in European Application No. 07742677.3.
Atta Behfar et al., "Stem Cell Differentiation Requires a Paracrine Pathway in the Heart", The FASEB Journal, Oct. 2002, pp. 1558-1566, vol. 16.
Jing Hao et al., "WNT/β-Catenin Pathway Up-Regulates *Stat3* and Converges on LIF to prevent differentiation of mouse embryonic stem cells", Developmental Biology, 2006, pp. 81-91, vol. 290.
Izhak Kehat et al., "Human Embryonic Stem Cells Can Differentiate into Myocytes with Structural and Funtional Properties of Cardiomyocytes", The Jouranl of Clinical Investigation, Aug. 2001, pp. 407-414, vol. 108, No. 3.
Michael G. Klug et al., "Genetically Selected Cardiomyocytes From Differentiating Embryonic Stem Cells Form Stable Intracardiac Grafts", J. Clin. Invest., Jul. 1996, pp. 216-224, vol. 98, No. 1.
Masamichi Koyanagi et al., "Non-Canonical Wnt Signaling Enhances Differentiation of Human Circulating Progenitor Cells to Cardiomyogenic Cells", The Journal of Biological Chemistry, Apr. 29, 2005, pp. 16838-16842, vol. 280, No. 17, Published by JBC Papers.
Michael Kühl et al., "The Wnt/$Ca^{2+}$ Pathway a New Vertebrate Wnt Signaling Pathway Takes Shape", The Wnt/$Ca^{2+}$ Pathway, Trends in Genetics, vol. 16, No. 7, pp. 279-283 (2000).
Jian Li et al., "Calreticulin Reveals a Critical $Ca^{2+}$ Checkpoint in Cardiac Myofibrillogenesis", The Journal of Cell Biology, Jul. 8, 2002, pp. 103-113, vol. 158, No. 1.
Victor A. Maltsev et al., "Cardiomyocytes Differentiated in Vitro From Embryonic Stem Cells Developmentally Express Cardiac-Specific Genes and Ionic Currents", Circulation Research, Aug. 1994, pp. 233-244, vol. 75, No. 2.
Victor A. Maltsev et al., "Embryonic Stem Cells Differentiate in Vitro into Cardiomyocytes Representing Sinusnodal, Atrial and Ventricular Cell Types", Mechanisms of Development, 1993, pp, 41-50, vol. 44.
Martha J. Marvin et al., "Inhibition of Wnt Activity Induces Heart Formation From Posterior Mesoderm", Genes and Development, 2001, pp. 316-327, vol. 15.
Atsuhiko T. Naito et al., "Phosphatidylinositol 3-Kinase-Akt Pathway Plays a Critical Role in Early Cardiomyogenesis by Regulating Canonical Wnt Signaling", Circulation Research Journal of the American Heart Association, Jul. 22, 2005, pp. 144-151, vol. 97, Published by the American Heart Association, Dallas, Texas.
Atsuhiko T. Naito et al., "Developmental Stage-Specific Biphasic Roles of Wnt/β-Catenin Signaling in Cardiomyogenesis and Hematopoiesis", PNAS, Dec. 26, 2006, pp. 19812-19817, vol. 103, No. 52.

(Continued)

*Primary Examiner* — Nancy T Vogel
(74) *Attorney, Agent, or Firm* — Drinker Biddle & Reath LLP

(57) ABSTRACT

The present invention provides a method for inducing differentiation of cardiomyocytes efficiently and selectively from stem cells.
A method for inducing differentiation of cardiomyocytes from pluripotent stem cells, which comprises: (i) culturing the pluripotent stem cells in a culture medium containing no substance that promotes activation of the canonical Wnt signaling pathway during the time period between initiation of differentiation induction and 24 hours before the period of elevated canonical Wnt gene expression; and then (ii) culturing the pluripotent stem cells in a culture medium containing a substance that promotes activation of the canonical Wnt signaling pathway during a time period of 24 to 96 hours, starting from 24 to 0 hours before the period of elevated canonical Wnt gene expression.

15 Claims, 13 Drawing Sheets

OTHER PUBLICATIONS

Teruya Nakamura et al., "A Wnt-and β-Catenin-Dependent Pathway for Mammalian Cardiac Myogenesis", PNAS, May 13, 2003, pp. 5834-5839, vol. 100, No. 10.

Roel Nusse, "Wnt Signaling in Disease and in Development", Cell Research, Jan. 2005, pp. 28-32, vol. 15, No. 1.

Petra Pandur et al., "Wnt-11 Activation of a Non-Canonical Wnt Signalling Pathway is Required for Cardiogenesis", Nature, Aug. 8, 2002, pp. 636-641, vol. 418.

Agapios Sachinidis et al., "Cardiac Specific Differentiation of Mouse Embryonic Stem Cells", Cardiovascular Research, 2003, pp. 278-291, vol. 58.

Heinrich Sauer et al., "Role of Reactive Oxygen Species and Phosphatidylinositol 3-Kinase in Cardiomyocyte Differentiation of Embryonic Stem Cells", FEBS Letters, 2000, pp. 218-223, vol. 476.

Valerie A. Schneider et al., "Wnt Antagonism Initiates Cardiogenesis in *Xenopus laevis*", Genes & Development, 2001, pp. 304-315, vol. 15.

Michael J. Shamblott et al, "Derivation of Pluripotent Stem Cells From Cultured Human Primordial Germ Cells", Proc. Natl. Acad. Sci., Nov. 1998, pp. 13726-13731, vol. 95.

Mark H. Soonpaa et al., "Formation of Nascent Intercalated Disks Between Grafted Cardiomyocytes and Host Myocardium", Science, Apr. 1, 1994, pp. 98-101, vol. 264.

Tomosaburo Takahashi et al., "Ascorbic Acid Enhances Differentiation of Embryonic Stem Cells into Cardiac Myocytes", Circulation Journal of the American Heart Association, 2003, pp. 1912-1916, vol. 107, Published by the American Heart Association, Dallas, Texas.

Hiromi Terami et al., "Wnt11 Facilitates Embryonic Stem Cell Differentiation to Nkx2.5-positive Cardiomyocytes", Biochemical and Biophysical Research Communications, 2004, vol. 325, No. 3, pp. 968-975.

James A. Thomson et al., "Embryonic Stem Cell Lines Derived From Human Blastocysts", Science, Nov. 6, 1998, pp. 1145-1147, vol. 282.

James A. Thomson et al., "Isolation of a Primate Embryonic Stem Cell Line", Proc. Natl. Acad. Sci., Aug. 1995, pp. 7844-7848, vol. 92.

Ai-Sun Tseng et al., "The GSK-3 Inhibitor BIO Promotes Proliferation in Mammalian Cardiomyocytes", Chemistry & Biology, Sep. 2006, pp. 957-963, vol. 13.

Carlo Ventura et al., "Dynorphin B is an Agonist of Nuclear Opioid Receptors Coupling Nuclear Protein Kinase C Activation to the Transcription of Cardiogenic Genes in GTR1 Embryonic Stem Cells", Circulation Research Journal of the American Heart Association, Apr. 4, 2003, pp. 623-629, vol. 92, Published by the American Heart Association, Dallas, Texas.

Randall Widelitz, "Wnt Signaling Through Canonical and Non-Canonical Pathways: Recent Progress", Growth Factors, Jun. 2005, pp. 111-116, vol. 23, No. 2.

Anna M. Wobus et al., "Retinoic Acid Accelerates Embryonic Stem Cell-Derived Cardiac Differentiation and Enhances Development of Ventricular Cardiomyocytes", J Mol Cell Cardiol, 1997, pp. 1525-1539, vol. 29.

Chunhui Xu et al., "Characterization and Enrichment of Cardiomyocytes Derived From Human Embryonic Stem Cells", Circulation Research Journal of the American Heart Association, Sep. 20, 2002, pp. 501-508, vol. 91, Published by the American Heart Association, Dallas, Texas.

Jun K. Yamashita et al., "Prospective Identification of Cardiac Progenitors by a Novel Single Cell-Based Cardiomyocyte Induction", The FASEB Journal, 2005, pp. 1-29.

Shinsuke Yuasa et al. "Transient Inhibition of BMP Signaling by Noggin Induces Cardiomyocyte Differentiation of Mouse Embryonic Stem Cells", Nature Biotechnology, May 2005, pp. 607-611, vol. 23, No. 5.

International Search Report issued on May 29, 2007 in International PCT Application No.PCT/JP2007/059242 filed Apr. 24, 2007.

Nakatsuji et al., "Embryonic Stem Cell Lines of Nonhuman Primates," The ScientificWorldJournal, (2002), vol. 2, pp. 1762-1773.

Schwanke et al., "Generation and Characterization of Functional Cardiomyocytes from Rhesus Monkey Embryonic Stem Cells," Stem Cells, (2006); vol. 24, pp. 1423-1432.

Lindsley et al., "Canonical Wnt signaling is required for development of embryonic stem cell-derived mesoderm," Development 133, (2006), pp. 3787-3796.

Ueno et al., "Biphasic role for Wnt/β-catenin signaling in cardiac specification in zebrafish and embryonic stem cells," PNAS, Jun. 5, 2007, vol. 104, No. 23, pp. 9685-9690.

Kwon et al., "Canonical Wnt signaling is a positive regulator of mammalian cardiac progenitors," PNAS, Jun. 26, 2007, vol. 104, No. 26, pp. 108994-10899.

Palpant et al., "Non-canonical Wnt Signaling Enhances differentiation of Sca1$^+$/c-kit$^+$ Adipose-derived Murine Stromal Vascular Cells into Spontaneously Beating Cardiac Myocytes," J. Mol. Cell Cardiol. Sep. 2007, vol. 43, No. 3, pp. 362-370.

Anton et al., "β-Cantenin signaling contributes to stemness and regulates early differentiation in murine embryonic stem cells," FEBS Letters 581 (2007) pp. 5247-5254.

Tran et al., "Wnt3a-induced Mesoderm Formation and Cardiomyogenesis in Human Embryonic Stem Cells," Stem Cells (2009) vol. 27, pp. 1869-1878.

Paige et al., "Ednogenous Wnt/β-/Cantenin Signaling is Required for Cardiac Differentiation in Human Embryonic Stem Cells," PLoS One, Jun. 2010, vol. 5, Issue 6, e11134.

European Office Action dated Aug. 5, 2011 in EP Application No. 07 742 677.3.

Sato et al., "Maintenance of pluripotency in human and mouse embryonic stem cells through activation of Wnt signaling by a pharmacological GSK-3-specific inhibitor," Nature Medicine, vol. 10, No. 1, Jan. 2004, pp. 1-9.

\* cited by examiner

[Figure 1A]
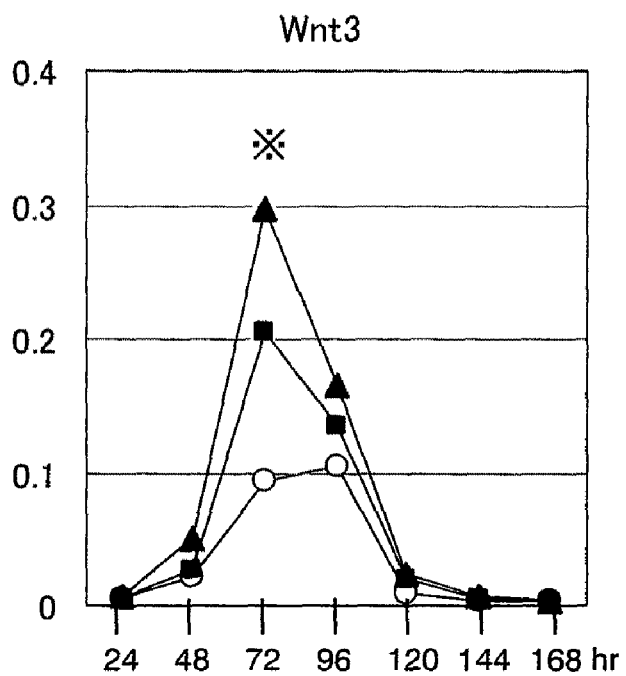
[Figure 1B]
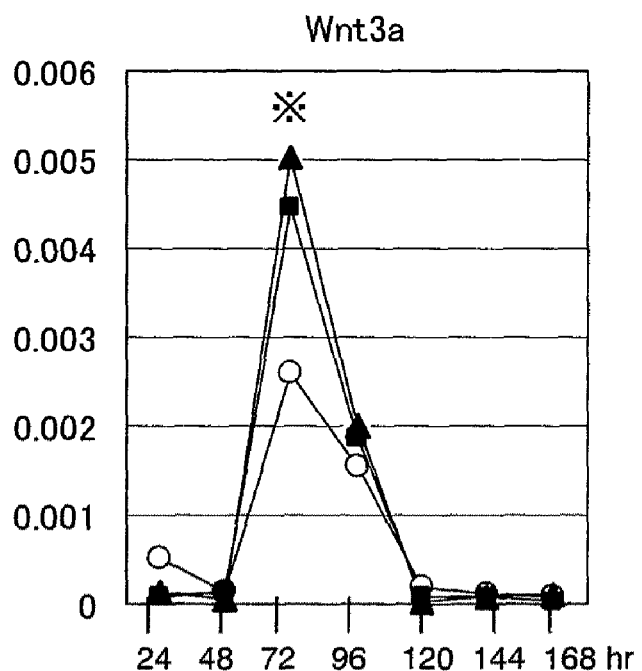

[Figure 1C]
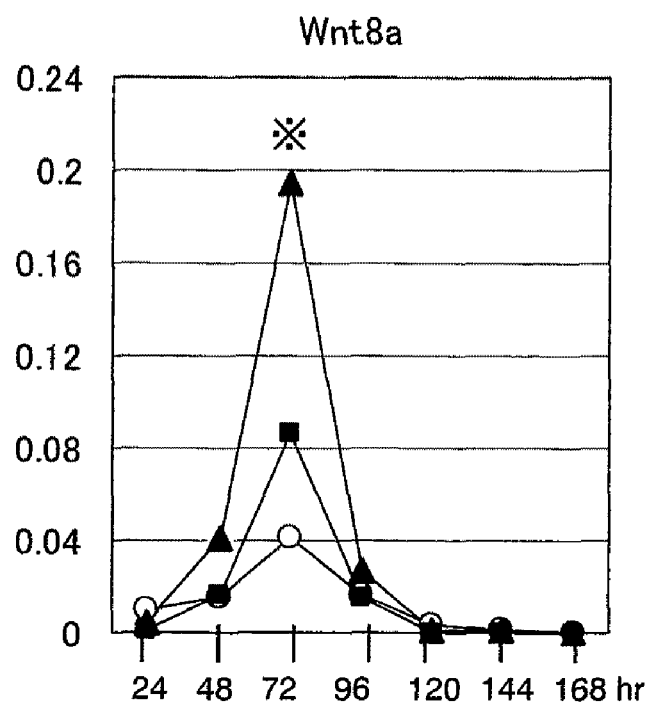

[Figure 2A]
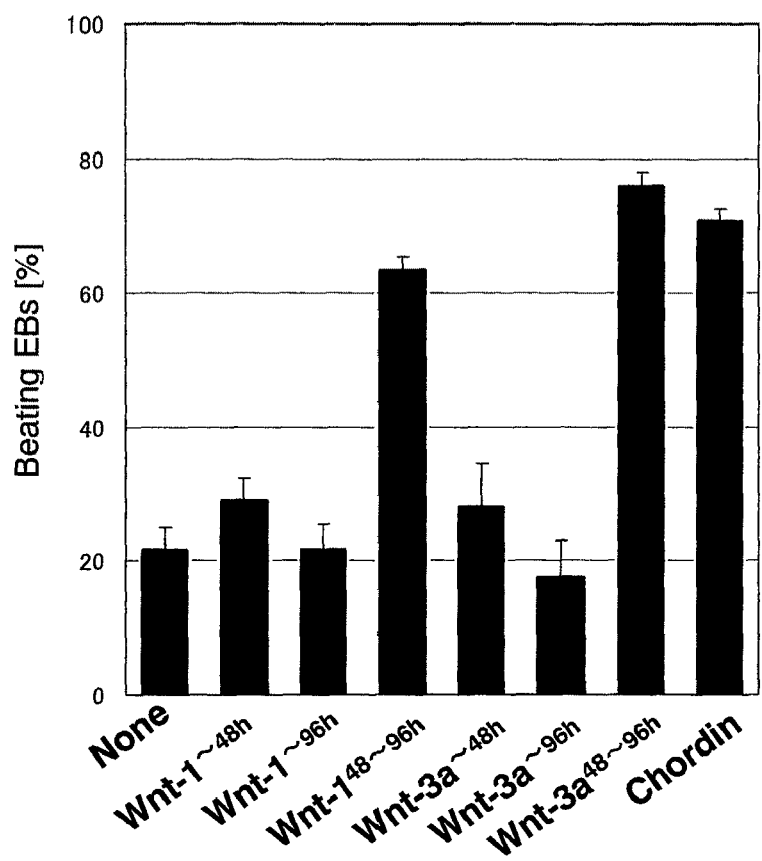

[Figure 2B]

| Treatment period | Hours after induction of differentiation | | | | | | | Appearance of beating EBs |
|---|---|---|---|---|---|---|---|---|
| | 24 | 48 | 72 | 96 | 120 | 144 | 168 | |
| None | | | | | | | | + |
| ~48h | ● | ● | | | | | | + |
| ~72h | ● | ● | ● | | | | | + |
| ~96h | ● | ● | ● | ● | | | | + |
| ~120h | ● | ● | ● | ● | ● | | | + |
| 48~96h | | | ● | ● | | | | +++ |
| 48~120h | | | ● | ● | ● | | | +++ |
| 120h~ | | | | | ● | ● | ● | + |
| 144h~ | | | | | | ● | ● | + |
| All | ● | ● | ● | ● | ● | ● | ● | + |

[Figure 3A]
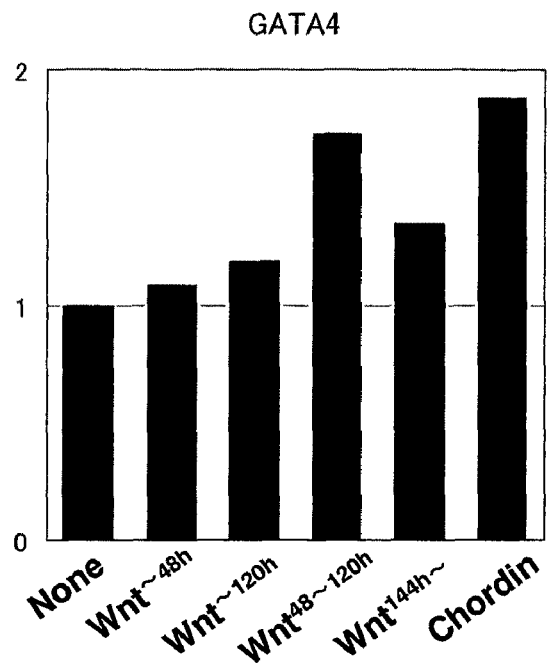
[Figure 3B]
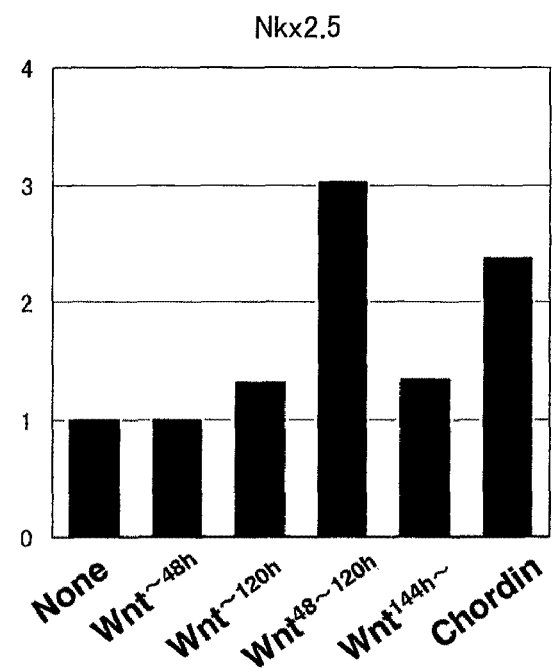

[Figure 3C]
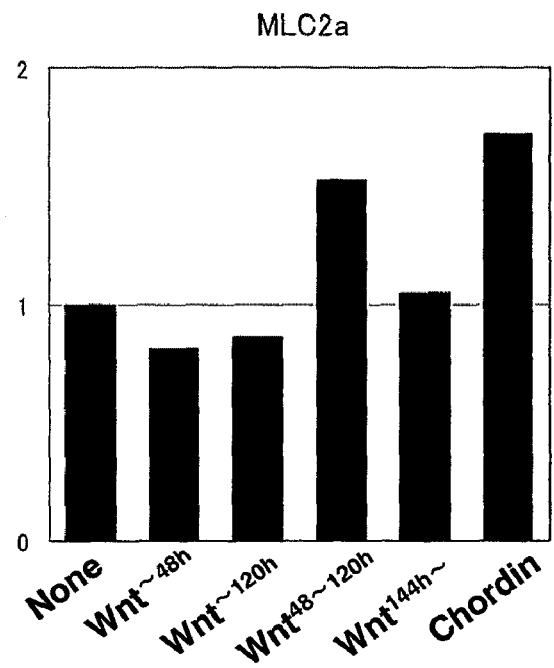
[Figure 3D]
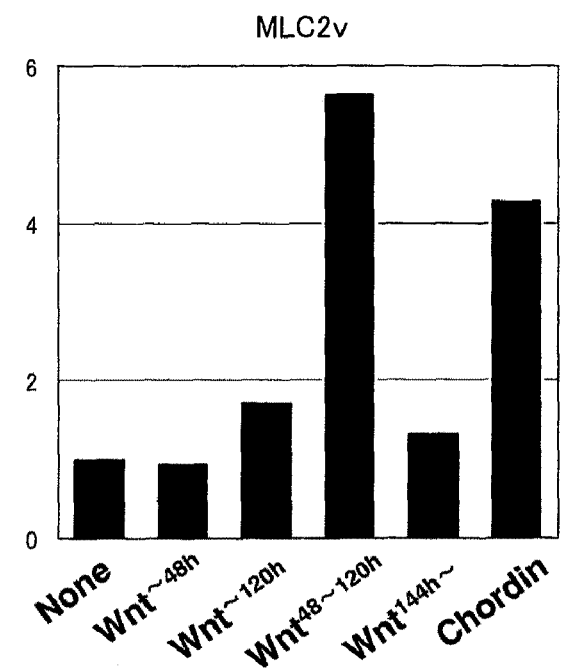

[Figure 4]
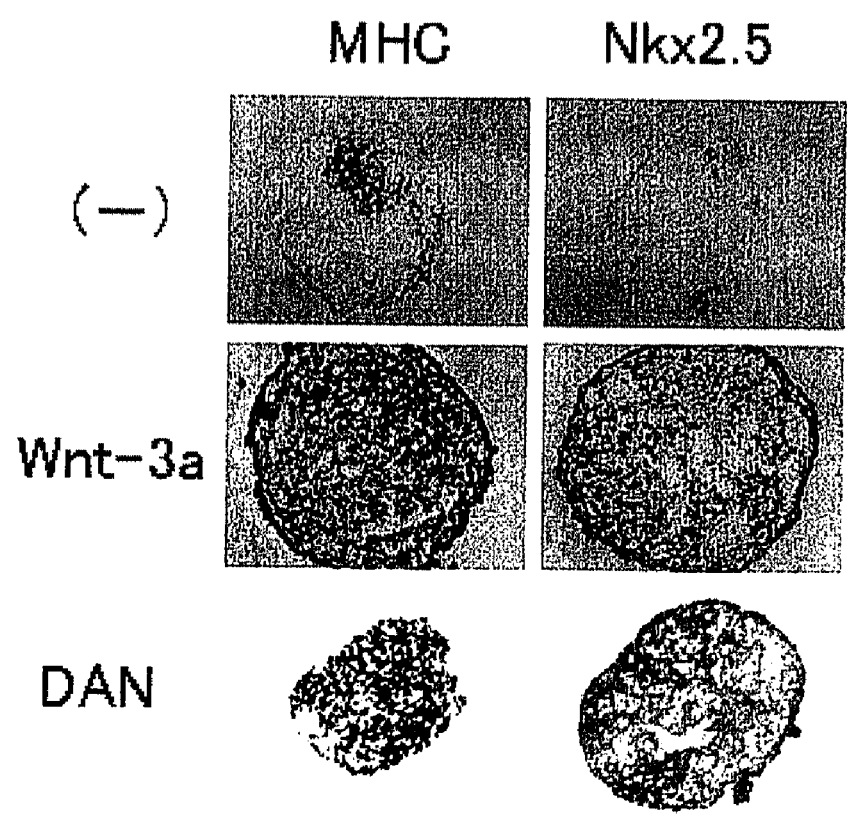

[Figure 5A]
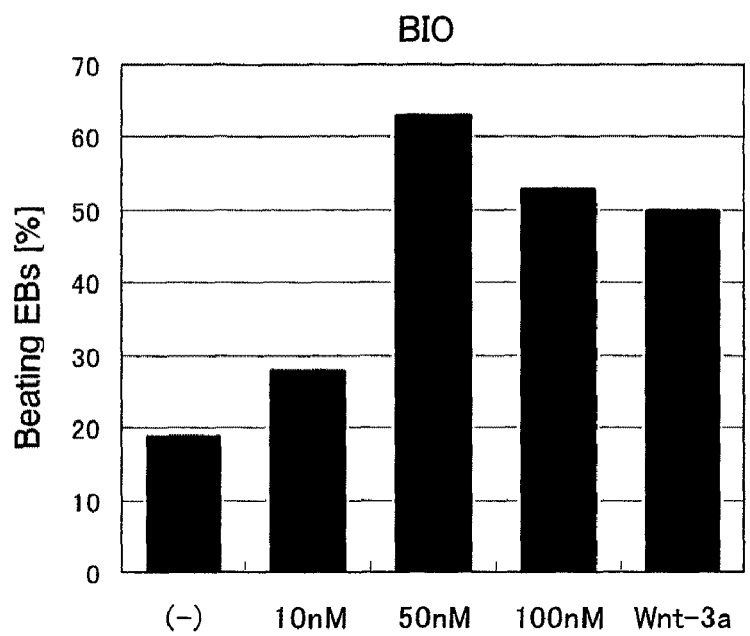
[Figure 5B]
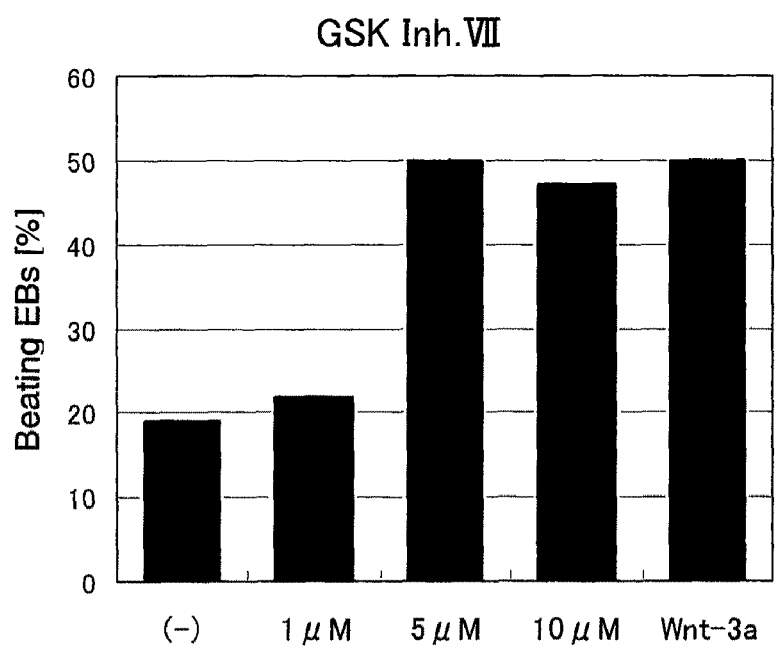

[Figure 5C]
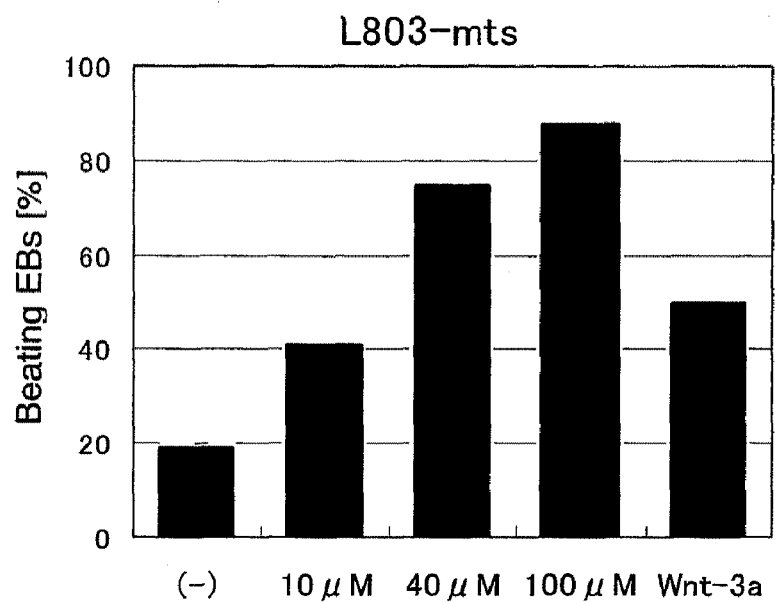
[Figure 5D]
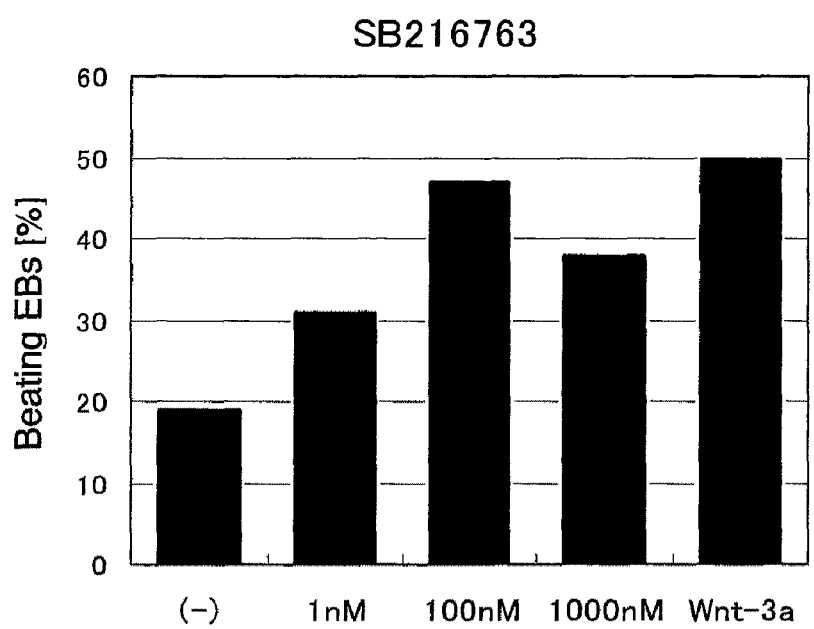

[Figure 5E]
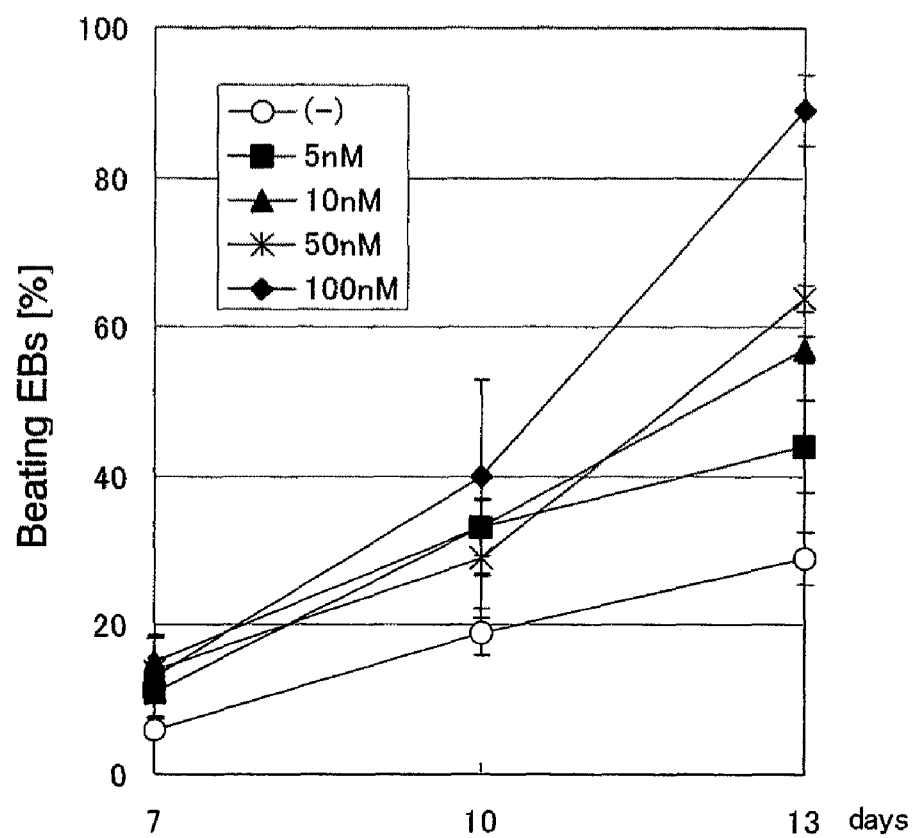

[Figure 6]
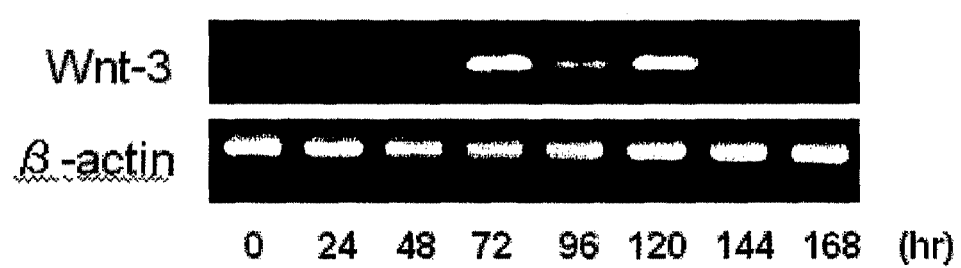

[Figure 7]
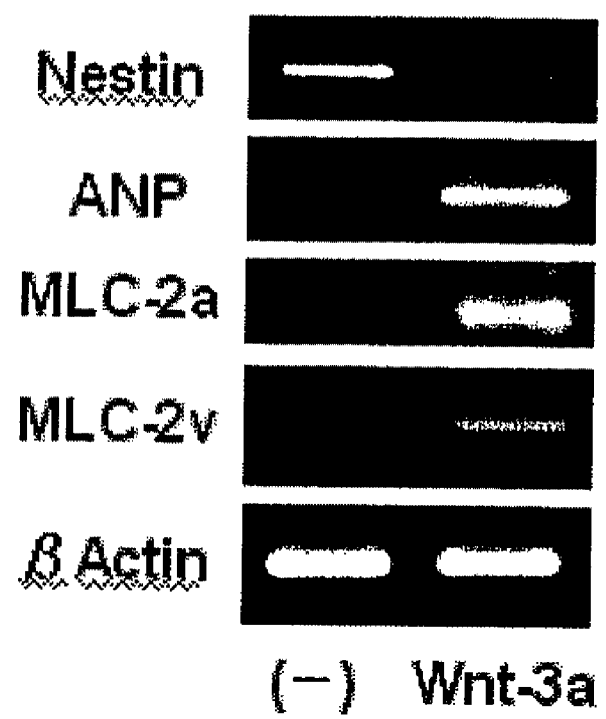

[Figure 8]
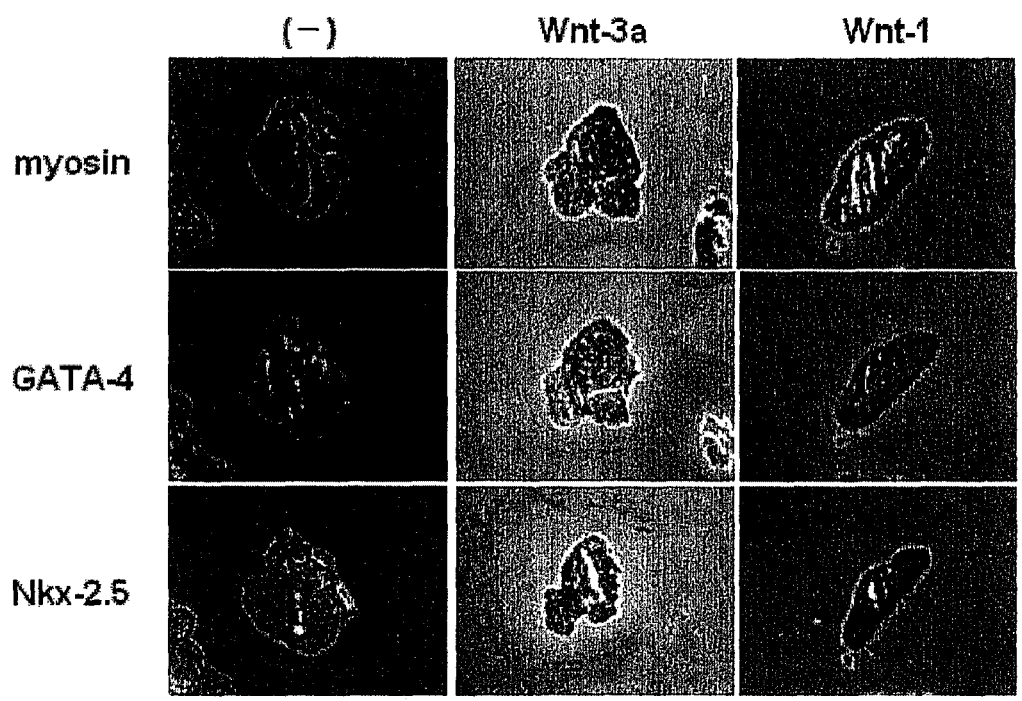

METHOD FOR INDUCING DIFFERENTIATION OF PLURIPOTENT STEM CELLS INTO CARDIOMYOCYTES

CROSS REFERENCE TO RELATED APPLICATIONS

This application is the National Stage of International Application No. PCT/JP2007/059242, filed Apr. 27, 2007, and claims benefit of Japanese Application Nos. 2006-125148, filed Apr. 28, 2006 and 2007-19531 filed Jan. 30, 2007, both of which are herein incorporated by reference in their entirety.

REFERENCE TO A SEQUENCE LISTING

A Sequence Listing containing SEQ ID NO: 1-39 is incorporated herein by reference.

TECHNICAL FIELD

The present invention relates to a method for preparing cardiomyocytes selectively and efficiently from ES cells and other pluripotent stem cells.

BACKGROUND ART (1) Preparation of Cardiomyocytes Using Pluripotent Stem Cells In general, cardiomyocytes undergo active cell division with beating autonomously before birth, but immediately after birth they lose the ability to divide, and since they have very few undifferentiated stem cells and precursor cells whose growth and differentiation abilities are extremely low, when cardiomyocytes die due to exposure to various forms of stress including myocardial infarction, myocarditis and the like, the lost cardiomyocytes cannot be regenerated. As a result, the surviving cardiomyocytes try to maintain myocardial function through compensatory hypertrophy and the like, but if the stress continues and exceeds an allowable threshold, it leads to further exhaustion and death of cardiomyocytes and a consequent lowering of myocardial function (that is, heart failure).

Heart failure and other types of heart disease are the second leading cause of death in Japan, and prognoses are very poor, with a 5-year survival rate of only about 50% for patients with heart diseases. Therefore, it is hoped that development of highly effective therapies for heart failure will lead to great advances in medical welfare as well as improved medical economics. Conventional therapeutic drugs for heart failure include digitalis preparations that increase the contractive force of the myocardium and xanthine preparations and other heart stimulants, but long-term administration of these drugs is known to make the condition worse because there is too much expenditure of myocardial energy. More recently, mainstream therapy has shifted to β-blockers and ACE inhibitors, which reduce the excess burden on the heart due to stimulation of the sympathetic nervous system and renin-angiotensin system, but these methods only deal with the immediate symptoms and cannot restore damaged cardiac tissue. By contrast, heart transplantation is a fundamental treatment for severe heart failure, but it is one that is difficult to apply commonly because of such problems as the shortage of heart donors, ethical concerns, the physical and financial burden on patients and the like.

Therefore, it would seem that methods of transplantation to replace weakened or lost cardiomyocytes would be extremely useful for the treatment of heart failure. In fact, it is known from animal experiments that when immature cardiomyocytes obtained from fetuses are transplanted into adult cardiac tissue, the transplanted cells function effectively (See Non-Patent Document 1). However, it is difficult to obtain sufficient cardiomyocytes for this method, and application to clinical medicine is also difficult from an ethical standpoint.

Attention has therefore focused in recent years on inducing differentiation of stem cells into cardiomyocytes and using these cells for transplantation. At present it has not yet been possible to clearly identify a population of precursor cells or stem cells capable of producing cardiomyocytes in adult cardiac tissue, so pluripotent stem cells, which are less differentiated and can differentiate into a variety of cells, are considered to be useful for the above method.

Pluripotent stem cells are defined as cells which are capable of indefinite or long-term cell proliferation while remaining in an undifferentiated state in an in vitro culture, which retain normal karyotypes, and which have the ability to differentiate into all of three germ layers (ectoderm, mesoderm and endoderm) under appropriate conditions. The three well-known pluripotent stem cells are embryonic stem cells (ES cells) derived from early-stage embryos, embryonic germ cells (EG cells) derived from primordial germ cells at the embryonic stage, and germline stem cells (GS cells) derived from testes immediately after birth.

In particular, it has long been known that ES cells can be induced to differentiate into cardiomyocytes in vitro. Mouse ES cells were used in most of the early studies. When ES cells are cultured in suspension culture as single cells (individual cells dispersed with no adhesion between cells due to enzyme treatment or the like) without the presence of a differentiation-inhibiting factor such as leukemia inhibitory factor (LIF) or the like, the ES cells adhere to one another and aggregate, forming a structure called embryoid bodies (EBs) which are similar to the early embryonal structures. It is also known that cardiomyocytes with spontaneous beating ability appear when these EBs are cultured in suspension or in adhesion on the surface of culture devices.

ES cell-derived cardiomyocytes prepared as described above exhibit very similar properties to those of immature cardiomyocytes in fetal hearts (See Non-Patent Documents 2 and 3). Moreover, it has been confirmed from animal experiments that when ES cell-derived cardiomyocytes are actually transplanted into adult cardiac tissues, they are highly effective, with results similar to those obtained by transplantation of fetal myocardium (See Patent Document 1; Non-Patent Document 4).

In 1995, Thomson et al. first established ES cells from primates (See Patent Document 2; Non-Patent Document 5), and thus the regeneration therapy using pluripotent stem cell-derived cardiomyocytes has become realistic. Subsequently they also succeeded in isolating and establishing human ES cell lines from early human embryos (See Non-Patent Document 6). Moreover, Gearhart et al. established human EG cell lines from human primordial germ cells (See Non-Patent Document 7; Patent Document 3).

Kehat et al. (See Non-Patent Document 8) and Xu et al. (See Patent Document 4; Non-Patent Document 9) have reported that human ES cells can differentiate into cardiomyocytes in vitro, as mouse ES cells can do. According to these reports, cardiomyocytes derived from human ES cells not only have the ability to beat spontaneously but also express and produce myocardial-specific proteins such as myosin heavy and light chains, α-actinin, troponin I and atrial natriuretic peptide (ANP) and myocardial-specific transcription factors such as GATA-4, Nkx2.5, MEF-2c and the like, and from microanatomical observation and electrophysiological analysis it appears that they retain the properties of immature cardiomyocytes at the fetal stage, and could be used for regenerative therapy.

However, one serious problem remains to be elucidated to use pluripotent stem cell-derived cardiomyocytes for cell transplantation therapy and other purposes. When EBs are formed from ES cells or EG cells by conventional methods, not only cardiomyocytes, but also other types of differentiated cells, such as blood cells, vascular cells, neural cells, intestinal cells, bone and cartilage cells and the like, are developed. Moreover, the proportion of cardiomyocytes in these differentiated cell population is not so high, only about 5% to 20% of the total.

Methods of isolating only cardiomyocytes from a mixture of various kinds of cells include a method of adding an artificial modification to the ES cell genes, conferring drug resistance or ectopic expression, and collecting cells having the properties of cardiomyocytes or precursor cells thereof. For example, by introducing a gene cassette capable of expressing a neomycin (G418) resistance gene under the control of the α-myosin heavy chain promoter into mouse ES cells, Field and his co-researchers established a system in which those ES cells could only survive in medium to which G418 had been added when they differentiated into cardiomyocytes and expressed the α-myosin heavy chain gene (See Patent Document 1; Non-Patent Document 4). 99% or more of G418-resistant cells selected by this method were confirmed to be cardiomyocytes. However, although the purity of the cardiomyocytes is extremely high in this method, the final number of cardiomyocytes obtained is only a few percent of the total cell count, making it difficult to obtain enough amounts of cardiomyocytes for transplantation.

Xu et al. have reported that when human ES cells are treated with 5-azacytidine, the percentage of troponin I-positive cells (candidate cardiomyocytes) in EBs rises from 15% to 44% (See Non-Patent Document 9), but even in this method the percentage of cardiomyocytes in EBs does not exceed 50%. Moreover, 5-azacytidine is a demethylation agent that alters the expression of genes by removing methyl groups bound to DNA, and because it acts directly on the chromosomes, it is not a suitable drug for preparing cells for cell transplantation.

Other methods for producing cardiomyocytes more efficiently from ES cells include, in the case of mouse ES cells, addition of retinoic acid (See Non-Patent Document 10), ascorbic acid (See Non-Patent Document 11), TGFβ, BMP-2 (See Non-Patent Document 12), PDGF (See Non-Patent Document 13) and Dynorphin B (See Non-Patent Document 14) and treatment to increase reactive oxygen species (ROS) (See Non-Patent Document 15) and $Ca^{2+}$ (See Non-Patent Document 16) in the cells, all of which are known to act positively to induce cardiomyocyte differentiation. However, cardiomyocyte-specific or selective differentiation has not been achieved with any of these methods. Recently, the research group including the inventors has shown that when ES cells are transiently treated with a BMP antagonist, differentiation into cardiomyocytes can be induced more efficiently and selectively than in conventional methods (Patent Document 5; Non-Patent Document 17).

(2) Functional Roles of Wnt Proteins During Differentiation and Development of Cardiomyocytes Wnt proteins, which are secretory proteins, are members of a protein family group whose presence is widely found not only in vertebrate animals, but also in invertebrate animals such as nematodes and insects, and their gene family is known to have many molecular species (Non-Patent Documents 18 and 19). For example, 19 Wnt genes (Wnt-1, 2, 2b/13, 3, 3a, 4, 5a, 5b, 6, 7a, 7b, 8a, 8b, 9a, 9b, 10a, 10b, 11, 16) have been identified in humans and mice so far. Wnt proteins encoded by these Wnt genes have different tissue specificity, but are structurally similar to each other.

When Wnt proteins contribute as ligands to the intracellular signaling systems, they bind to the seven-transmembrane Frizzled (hereinafter abbreviated as Fzd) family of receptors present on the cell membrane. There are several pathways acting downstream of Fzd receptors, and the most major pathway is inhibition of β-catenin phosphorylation mediated by glycogen synthase kinase (GSK)-3β. In the absence of Wnt signals, β-catenin is captured together with GSK-3β by Axin on Adenomatous polyposis coli (APC) protein and is rapidly phosphorylated by GSK-3β. The phosphorylated β-catenin undergoes ubiquitination and proteasome-mediated degradation.

On the other hand, when Wnt proteins bind to Fzd receptors, an intracellular factor Dishevelled is activated to capture GSK-3β, whereby β-catenin is not phosphorylated and remains in free form within the cytoplasm and further migrates into the nucleus. After migrating into the nucleus, β-catenin binds to lymphoid enhancer factor-1/T cell factor (hereinafter abbreviated as LEF-1/TCF) present in the nucleus to form a transcription activator complex, thereby inducing transcription of a target gene. Such a signaling pathway involving accumulation and nuclear migration of β-catenin is called the "classical" Wnt pathway or the canonical Wnt signaling pathway, and a family of molecular species (e.g., Wnt-1, Wnt-3a, Wnt-8a) capable of activating this pathway is referred to as canonical Wnt. It is also known that activation of the canonical Wnt signaling pathway is induced by treatment with various GSK-3β inhibitors.

Wnt ligands are known to activate not only the β-catenin pathway but also other signaling pathways through Fzd receptors. Such signaling pathways include the planar cell polarity (PCP) pathway which activates JNK (Jun N-terminal kinase), a kind of MAP kinase, and the $Ca^{2+}$ pathway which elevates the intracellular $Ca^{2+}$ concentration and activates protein kinase C through trimeric G protein activation and the subsequent phospholipase C activation (Non-Patent Documents 19 and 20). These pathways are called "non-classical" Wnt pathways or non-canonical Wnt signaling pathways, in contrast to the canonical Wnt signaling pathway. Wnt-4 and Wnt-11 have been reported to be Wnt family molecules capable of activating such pathways, and these Wnt ligands act to inhibit the canonical Wnt signaling pathway.

It should be noted that some molecular species of Wnt protein have the ability to activate both canonical and non-canonical pathways, depending on the type of target cells and their differentiation stage, as well as differences in Fzd receptors expressed in the target cells. For example, Wnt-5a is known to act as non-canonical Wnt in commonly used assay systems such as secondary axis formation in *Xenopus laevis* embryos and carcinogenesis of mammary gland epithelial cells, whereas Wnt-5a has also been reported to induce stabilization of β-catenin and its transcription activity in ES cells, i.e., to activate the canonical Wnt signaling pathway in ES cells (Non-Patent Document 21).

Wnt proteins are known to be involved in a wide variety of biological functions during development, growth and differentiation of various cells, tissues and cancers. Cardiomyocytes develop from a part of the lateral plate mesoderm at the early stage of development, and then repeatedly divide and grow to form a heart. The presence or absence of Wnt signals plays an important role in this process, as demonstrated in several cases. By way of example, in the early stage of avian or *Xenopus laevis* development, ectopic and/or forced expression of the Wnt-3a or Wnt-8a gene which activates the canonical Wnt signaling pathway significantly inhibits heart formation (Non-Patent Documents 22 and 23).

On the other hand, so-called Wnt antagonists (e.g., Frzb, Dkk-1) which bind to Wnt-3a or Wnt-8a to inhibit its signaling promote heart formation, thus suggesting that canonical Wnt signals act to inhibit myocardial development.

On the contrary, activation of non-canonical Wnt signaling pathways which antagonize canonical Wnt signals is known to positively induce development and differentiation of cardiomyocytes. Pandur et al. (Non-Patent Document 24) have shown that Wnt-11 which activates non-canonical pathways without activating the canonical pathway is a factor essential for heart development in *Xenopus laevis*. Thereafter, the promoting effect of Wnt-11 has also been confirmed in myocardial differentiation-inducing systems for mouse ES cells (Non-Patent Document 25) and human vascular endothelial precursor cells (Non-Patent Document 26). As to activation of non-canonical Wnt signaling pathways, it is also known that cardiomyocytes can be induced to differentiate from cells of tongue tissue (Patent Document 6).

On the other hand, unlike the above cases, it is known that activation of the canonical Wnt signaling pathway acts to promote myocardial differentiation from embryonic carcinoma cells (EC cells). P19CL6 cells, a subline of P19 cells which are a kind of EC cells, have the property of differentiating into cardiomyocytes under stimulation with dimethyl sulfoxide (DMSO). When Wnt-3a or Wnt-8 was added to medium, P19CL6 cells were promoted to differentiate into cardiomyocytes as β-catenin was stabilized (Non-Patent Document 27). In this system, it is also shown that the time period sufficient for Wnt protein addition is 4 days immediately after induction of differentiation (Non-Patent Document 28).

P19 cell lines have characteristics partially similar to those of ES cells in that they can be induced to differentiate into cardiomyocytes and neurons. However, P19 cell lines do not have the ability to differentiate into a variety of cells or the ability to form chimeras, unlike ES cells. Moreover, P19 cell lines greatly differ from ES cells in terms of cell surface markers, expressed genes and so on. Namely, P19 cell lines may be used as a model system for ES cells in certain experiments, but do not always have the same characteristics as ES cells. Thus, it was not possible to predict, based on scientific grounds, whether the findings obtained in this experimental system could be directly extrapolated to myocardial differentiation-inducing systems for ES cells and other pluripotent stem cells.

Recently, in experimental systems using mouse ES cells, Wnt-3a protein, a member of canonical Wnt, has been reported to promote myocardial differentiation from ES cells when added for 3 days after initiation of differentiation induction (Naito A et al., 28th Annual Meeting of the Molecular Biology Society of Japan, 2005 Dec. 7 to 2005 Dec. 10, Hakata, Japan; Non-Patent Document 30). However, similar studies carried out by us have indicated that there is no significant promoting effect on differentiation (Example 2), and other research groups have also reported that treatment of mouse ES cells with Wnt-3a produces no particularly significant effect on induction of myocardial differentiation (Non-Patent Document 25) or produces an inhibitory effect on myocardial differentiation (Non-Patent Document 29). Namely, it is not clear how activated canonical Wnt pathway caused on myocardial differentiation from ES cells or other pluripotent stem cells. Under these circumstances, no optimum culture method has been established for inducing myocardial differentiation.

Patent Document 1: U.S. Pat. No. 6,015,671
Patent Document 2: U.S. Pat. No. 5,843,780
Patent Document 3: U.S. Pat. No. 6,090,622
Patent Document 4: WO03/06950
Patent Document 5: WO2005/033298
Patent Document 6: JP 2005-224155 A
Non-Patent Document 1: Soonpaa M H et al., Science, 264: 98, 1994
Non-Patent Document 2: Maltsev V A et al., Mechanism of Development, 44:41, 1993
Non-Patent Document 3: Maltsev V A et al., Circulation Research, 75:233, 1994
Non-Patent Document 4: Klug M G et al., Journal of Clinical Investigation, 98:216, 1996
Non-Patent Document 5: Thomson J A et al., Proceedings of the National Academy of Sciences of the United States of America, 92:7844, 1995
Non-Patent Document 6: Thomson J A et al., Science, 282: 1145, 1998
Non-Patent Document 7: Shamblott M J et al., Proceedings of the National Academy of Sciences of the United States of America, 95:13726, 1998
Non-Patent Document 8: Kehat I et al., Journal of Clinical Investigation, 108:407, 2001
Non-Patent Document 9: Xu C et al., Circulation Research, 91:501, 2002
Non-Patent Document 10: Wobus A M et al., Journal of Molecular and cellular Cardiology, 29:1525, 1997
Non-Patent Document 11: Takahashi T et al., Circulation, 107:1912, 2003
Non-Patent Document 12: Behfar A et al., FASEB Journal, 16:1558, 2002
Non-Patent Document 13: Sachinidis et al., Cardiovascular Research, 58:278, 2003
Non-Patent Document 14: Ventura C et al., Circulation Research, 92:623, 2003
Non-Patent Document 15: Sauer H et al., FEBS Letters, 476: 218, 2000
Non-Patent Document 16: Li J et al., Journal of Cell Biology, 158:103, 2002
Non-Patent Document 17: Yuasa S et al., Nature Biotechnology, 23:607, 2005
Non-Patent Document 18: Nusse R, Cell Research, 15:28,
Non-Patent Document 19: Widelitz R, Growth Factors, 23:111, 2005
Non-Patent Document 20: Kühl M et al., Trends in Genetics, 16:279, 2000
Non-Patent Document 21: Hao J et al., Developmental Biology, 290:81, 2006
Non-Patent Document 22: Schneider V A & Mercola M, Genes and development, 15:304, 2001
Non-Patent Document 23: Marvin M J et al., Genes and Development, 15:316, 2001
Non-Patent Document 24: Pandur P et al., Nature, 418:636, 2002
Non-Patent Document 25: Terami H et al., Biochemical and Biophysical Research Communication, 325:968, 2004
Non-Patent Document 26: Koyanagi M et al., Journal of Biological Chemistry, 280:16838, 2005
Non-Patent Document 27: Nakamura T et al., Proceedings of the National Academy of Sciences of the United States of America, 100:5834, 2003
Non-Patent Document 28: Naito A T et al., Circulation Research, 97:144, 2005

Non-Patent Document 29: Yamashita J K et al., FASEB Journal, 19:1534, 2002

Non-Patent Document 30: Naito A T et al., Proceedings of the National Academy of Sciences of the United States of America, 103:19812, 2006

DISCLOSURE OF THE INVENTION

Problems to be Solved by the Invention

It is an object of the present invention to provide a method for inducing differentiation of undifferentiated pluripotent stem cells into cardiomyocytes efficiently and selectively by activating the canonical Wnt signaling pathway, along with cardiomyocytes obtained by this method and a method for using these cells in cell transplantation and injection and other therapies targeting heart disease.

Means for Solving the Problems

As the stem cell source for preparing cardiomyocytes, the inventors used pluripotent stem cells, especially ES cells, which were most commonly used, and as a result of extensive research into the conditions for inducing differentiation into cardiomyocytes or precursor cells thereof, they made the present invention when they discovered that when a substance that promotes activation of the canonical Wnt signaling pathway (hereinafter referred to as "Wnt signaling activator") was added to the medium during a certain, restricted stage of culture, populations of cells having beating ability which were identified as cardiomyocytes were developed much more selectively and efficiently than in commonly used methods.

Pluripotent stem cells that can be used in the present invention include ES cells, EG cells and GS cells derived from mammals such as mice, monkeys and humans, as well as all pluripotent stem cells that are characteristically similar to ES cells. In this case, characteristical similarity to ES cells is defined in terms of cell-biological properties unique to ES cells, such as the presence of ES cell-specific surface markers (antigen), the expression of ES cell-specific genes, or the ability to produce teratomas or chimera mice.

In the present invention, specific examples of a substance that promotes activation of the canonical Wnt signaling pathway include various canonical Wnt proteins, GSK-3β inhibitors, and other low molecular weight compounds capable of activating the canonical Wnt signaling pathway. It is also possible to use genes capable of activating the canonical Wnt signaling pathway, e.g., various canonical Wnt genes, as well as β-catenin gene or active mutants thereof which are modified to delete the N-terminal end or to replace GSK-3β phosphorylation sites with unphosphorylated amino acids.

In the present invention, canonical Wnt proteins are members of the Wnt family protein group and are defined as substances that bind to Fzd family receptors and inhibit GSK-3β-mediated phosphorylation of β-catenin to thereby promote stabilization of β-catenin and its transcription activation ability. Preferred canonical Wnt proteins in the present invention include, for example, Wnt-1, Wnt-3a, Wnt-5a and Wnt-8a, as well as those sharing an amino acid sequence homology of at least 80%, more preferably at least 90% with these proteins and having the ability to activate β-catenin.

One feature of the present invention is that ES cells or other pluripotent stem cells are transiently stimulated with a Wnt signaling activator, and while the stimulus method is not particularly limited, preferred is a method of culturing the cells in medium containing a canonical Wnt protein, for example, a recombinant protein thereof (hereinafter referred to as "recombinant Wnt protein") obtained by allowing a purified canonical Wnt gene to be expressed. A canonical Wnt protein to be used and a gene encoding the same are preferably derived from animals of the same species as that used to derive the pluripotent stem cells, but those derived from animals of another species can also be used. In the case of using a recombinant Wnt protein, the culture medium is sterilely removed and replaced with fresh medium containing the recombinant Wnt protein at a concentration of 0.1 ng/mL to 500 ng/mL, preferably 1 ng/mL to 200 ng/mL, more preferably 10 ng/mL to 100 ng/mL, and culture is continued.

GSK-3β inhibitors according to the present invention are defined as substances that inhibit the kinase activity of GSK-3β protein (e.g., the ability to phosphorylate (β-catenin); and more than several tens of inhibitors are already known. Specific examples include an indirubin derivative BIO (also called GSK-3β inhibitor IX; 6-bromoindirubin 3'-oxime), a maleimide derivative SB216763 (3-(2,4-dichlorophenyl)-4-(1-methyl-1H-indol-3-yl)-1H-pyrrole-2,5-dione), a phenyl-α-bromomethylketone compound GSK-3β inhibitor VII (4-dibromoacetophenone), and a cell-permeable phosphorylated peptide L803-mts (also called GSK-3β peptide inhibitor; Myr-N-GKEAPPAPPQSpP-$NH_2$ (SEQ ID NO: 40)). These compounds are commercially available from Calbiochem or Biomol and are easy to use, but this is not a limitation.

In a case where these GSK-3β inhibitors are used, their optimum concentration will vary greatly depending on differences in their properties of compounds. For this reason, it is necessary to determine the optimum concentration of each compound to be used. For example, in the case of BIO or SB216763, medium containing the GSK-3β inhibitor at a concentration of preferably 10 nmol/L to 1 μmol/L, more preferably 50 nmol/L to 200 nmol/L is used for medium replacement, and culture is continued. The concentration of GSK-3β inhibitor VII to be added is preferably 2 μmol/L to 100 μmol/L, and more preferably 5 μmol/L to 20 μmol/L. The concentration of L803-mts to be added is preferably 5 μmol/L to 500 μmol/L, more preferably 20 μmol/L to 200 μmol/L, and even more preferably 25 μmol/L to 200 μmol/L.

In addition to GSK-3β inhibitors, drugs for use in implementing the present invention may be low molecular weight compounds that promote activation of the canonical Wnt signaling pathway (hereinafter referred to as "Wnt agonists"). Preferred examples include an aminopyrimidine derivative (2-amino-4-[3,4-(methylenedioxy)benzyl-amino]-6-(3-methoxyphenyl)-pyrimidine; Calbiochem) (Liu et al., Angew. Chem. Int. Ed. Engl. 44:1987, 2005). In the case of using such a Wnt agonist, medium containing the Wnt agonist at a concentration of 1 nmol/L to 1000 nmol/L, preferably 10 nmol/L to 500 nmol/L, more preferably 50 nmol/L to 200 nmol/L is used for medium replacement, and culture is continued.

The timing of Wnt signaling activator treatment can be determined based on the expression patterns of various canonical Wnt genes during differentiation in pluripotent stem cells for use in implementing the present invention. More specifically, pluripotent stem cells are induced to differentiate in a routine manner, and mRNAs are extracted from the samples collected periodically to analyze the expression levels of various canonical Wnt genes by standard techniques such as RT-PCR. A time point at which the expression levels of the canonical Wnt genes are significantly elevated after induction of differentiation when compared to undifferentiated pluripotent stem cells is defined as the "period of elevated Wnt gene expression." Although a single canonical Wnt gene may be used for analysis, preferably two or more, more preferably three or more genes are desired.

In implementing the present invention, pluripotent stem cells are cultured in medium containing no Wnt signaling activator during the time period between immediately after initiation of culture for inducing myocardial differentiation and 24 hours before the period of elevated Wnt gene expression determined as described above. The pluripotent stem cells are further cultured in medium containing a Wnt signaling activator preferably for 24 to 96 hours, more preferably for 48 to 72 hours, starting from a time point of 24 to 0 hours before, preferably 24 hours before the period of elevated Wnt gene expression determined as described above. It should be noted that the time period during which the cells are treated with a Wnt signaling activator may vary to obtain an optimum period (hours), depending on differences in conditions such as the species of animal from which cells to be used are derived, the type of cell line to be used, and/or the type of Wnt signaling activator to be used.

Cardiomyocytes derived from ES cells or other pluripotent stem cells by the aforementioned method can be further collected, isolated and purified by known methods to efficiently obtain large quantities of highly pure cardiomyocytes. The cardiomyocytes thus obtained are hereinafter referred to as cardiomyocytes prepared according to the present invention.

Cardiomyocytes prepared according to the present invention are cells which exhibit the morphological, physiological and/or immunocytological characteristics of cardiomyocytes. In terms of physiological and/or immunocytological characteristics, cells prepared according to the present invention may express one or more markers specific to cardiomyocytes which are recognized as cardiomyocytes, but this is not a limitation.

Moreover, cardiomyocytes prepared according to the present invention can be used in methods of screening intended to identify potential chemotherapy drugs or novel factors which promote the development, differentiation, regeneration, survival and the like of cardiomyocytes.

Further, cardiomyocytes prepared according to the present invention can be used in methods for treating hearts suffering from cardiac disorders.

Namely, the present invention relates to, but is not limited to, the following.

(1) A method for inducing differentiation of cardiomyocytes from pluripotent stem cells, which comprises:

i) culturing the pluripotent stem cells in a culture medium containing no substance that promotes activation of the canonical Wnt signaling pathway during the time period between initiation of differentiation induction and 24 hours before the period of elevated canonical Wnt gene expression; and then ii) culturing the pluripotent stem cells in a culture medium containing a substance that promotes activation of the canonical Wnt signaling pathway during a time period of 24 to 96 hours, starting from 24 to 0 hours before the period of elevated canonical Wnt gene expression.

(2) The method according to (1) above, wherein the pluripotent stem cells are cultured in a culture medium containing a substance that promotes activation of the canonical Wnt signaling pathway, starting from 24 hours before the period of elevated canonical Wnt gene expression.

(3) The method according to (1) or (2) above, wherein the pluripotent stem cells are cultured in a culture medium containing a substance that promotes activation of the canonical Wnt signaling pathway during a time period of 48 to 72 hours.

(4) The method according to any one of (1) to (3) above, wherein the substance that promotes activation of the canonical Wnt signaling pathway is a substance selected from the group consisting of a canonical Wnt protein, a GSK3β inhibitor and a Wnt agonist.

(5) The method according to (4) above, wherein the substance that promotes activation of the canonical Wnt signaling pathway is a canonical Wnt protein.

(6) The method according to (5) above, wherein the canonical Wnt protein is at least one Wnt protein selected from the group consisting of Wnt-1, Wnt-3a and Wnt-5a.

(7) The method according to (5) or (6) above, wherein the concentration of the canonical Wnt protein in the culture medium is 0.1 ng/mL to 500 ng/mL.

(8) The method according to (4) above, wherein the substance that promotes activation of the canonical Wnt signaling pathway is a GSK3β inhibitor.

(9) The method according to (8) above, wherein the GSK3β inhibitor is at least one inhibitor selected from the group consisting of GSK3β inhibitor VII, L803-mts, SB216763 and GSK3β inhibitor IX (BIO).

(10) The method according to (8) or (9) above, wherein the concentration of the GSK3β inhibitor in the culture medium is 2 μmol/L to 100 μmol/L for GSK3β inhibitor VII, 5 μmol/L to 500 μmol/L for L803-mts, 10 nmol/L to 1 μmol/L for SB216763, or 10 nmol/L to 1 μmol/L for GSK3β inhibitor IX (BIO).

(11) The method according to (4) above, wherein the substance that promotes activation of the canonical Wnt signaling pathway is a Wnt agonist.

(12) The method according to (11) above, wherein the Wnt agonist is an aminopyrimidine derivative.

(13) The method according to (11) or (12) above, wherein the concentration of the Wnt agonist in the culture medium is 1 nmol/L to 1000 nmol/L.

(14) The method according to any one of (1) to (13) above, wherein the pluripotent stem cells are embryonic stem cells, embryonic germ cells or germline stem cells.

(15) The method according to (14) above, wherein the pluripotent stem cells are embryonic stem cells.

(16) The method according to (14) or (15) above, wherein the pluripotent stem cells are of human origin.

Advantages of the Invention

Myocardial precursor cells and cardiomyocytes can be very efficiently and selectively produced from ES cells and other pluripotent stem cells using the method of the present invention. Cardiomyocyte (precursor) cells prepared by the method of the present invention can be used to search for and develop effective drugs for treating heart disease, and could potentially be applied to myocardial transplantation therapy for severe heart disease.

BRIEF DESCRIPTION OF THE DRAWINGS

FIG. 1A shows changes in Wnt gene expression during induction of differentiation in ES cells. Symbols in the figure are defined as follows. Open circles: untreated group, solid squares: Chordin-treated group, solid triangles: DAN-treated group. The vertical axis represents the relative ratio of expression levels between the Wnt gene and the GAPBH gene used as an internal standard. Likewise, an asterisk (*) denotes a time point at which the expression level of the Wnt gene was significantly elevated as compared to undifferentiated ES cells.

FIG. 1B shows changes in Wnt gene expression during induction of differentiation in ES cells. Symbols in the figure are defined as follows. Open circles: untreated group, solid squares: Chordin-treated group, solid triangles: DAN-treated group. The vertical axis represents the relative ratio of expression levels between the Wnt gene and the GAPDH gene used as an internal standard. Likewise, an asterisk (*) denotes a time point at which the expression level of the Wnt gene was significantly elevated as compared to undifferentiated ES cells.

FIG. 1C shows changes in Wnt gene expression during induction of differentiation in ES cells. Symbols in the figure are defined as follows. Open circles: untreated group, solid squares: Chordin-treated group, solid triangles: DAN-treated group. The vertical axis represents the relative ratio of expression levels between the Wnt gene and the GAPDH gene used as an internal standard. Likewise, an asterisk (*) denotes a time point at which the expression level of the Wnt gene was significantly elevated as compared to undifferentiated ES cells.

FIG. 2A shows the effect on the appearance of beating EBs caused by differences in the timing of adding a recombinant Wnt protein to a culture medium.

FIG. 2B shows the effect on the appearance of beating EBs caused by differences in the timing of adding a recombinant Wnt protein to a culture medium.

FIG. 3A shows cardiomyocyte-specific marker gene expression in beating EBs which appeared after induction of differentiation in ES cells. The vertical axis represents the ratio relative to the gene expression level in the untreated group (None), which is set to 1.

FIG. 3B shows cardiomyocyte-specific marker gene expression in beating EBs which appeared after induction of differentiation in ES cells. The vertical axis represents the ratio relative to the gene expression level in the untreated group (None), which is set to 1.

FIG. 3C shows cardiomyocyte-specific marker gene expression in beating EBs which appeared after induction of differentiation in ES cells. The vertical axis represents the ratio relative to the gene expression level in the untreated group (None), which is set to 1.

FIG. 3D shows cardiomyocyte-specific marker gene expression in beating EBs which appeared after induction of differentiation in ES cells. The vertical axis represents the ratio relative to the gene expression level in the untreated group (None), which is set to 1.

FIG. 4 shows immunohistochemical staining of cardiomyocyte-specific marker proteins in beating EBs which appeared after induction of differentiation in ES cells.

FIG. 5A shows the effect of a GSK3β inhibitor on the appearance of beating EBs.

FIG. 5B shows the effect of a GSK3β inhibitor on the appearance of beating EBs.

FIG. 5C shows the effect of a GSK3β inhibitor on the appearance of beating EBs.

FIG. 5D shows the effect of a GSK3β inhibitor on the appearance of beating EBs.

FIG. 5E shows the effect of a GSK3β inhibitor on the appearance of beating EBs.

FIG. 6 shows changes in Wnt-3 gene expression during induction of differentiation in common marmoset (monkey) ES cells.

FIG. 7 shows cardiomyocyte-specific marker gene expression in beating EBs which appeared after induction of differentiation in cmES cells.

FIG. 8 shows immunohistochemical staining of cardiomyocyte-specific marker proteins in beating EBs which appeared after induction of differentiation in cmES cells.

MODES FOR CARRYING OUT THE INVENTION

Modes for carrying out the invention will be shown below, including the above effects of the present invention as well as other advantages and characteristics.

Anyone implementing the present invention can consult standard references regarding methods of genetic engineering such as molecular biology and recombinant DNA technology, as well as ordinary methods of cell biology and prior art, unless otherwise indicated. Such references include, for example, "Molecular Cloning: A Laboratory Manual, Third Edition" (Sambrook & Russell, Cold Spring Harbor Laboratory Press, 2001); "Current Protocols in Molecular biology" (Ausubel et al., eds., John Wiley & Sons, 1987); "Methods in Enzymology series" (Academic Press); "PCR Protocols: Methods in Molecular Biology" (Bartlett & Striling, eds., Humana Press, 2003); "Animal Cell Culture: A Practical Approach, Third Edition" (Masters, ed., Oxford University Press, 2000); and "Antibodies: A Laboratory Manual" (Harlow et al. & Lane, eds., Cold Spring Harbor Laboratory Press, 1987). The reagents and kits for cell culture and cell biological studies cited herein can be obtained from commercial sources including Sigma, Aldrich, Invitrogen/GIBCO, Clontech, Stratagene and the like.

Likewise, anyone implementing the present invention can consult standard references regarding ordinary methods of cell culture and developmental and cell biological studies using pluripotent stem cells. These include "Guide to Techniques in Mouse Development" (Wasserman et al., eds., Academic Press, 1993); "Embryonic Stem Cell Differentiation in vitro" (M. V. Wiles, Meth. Enzymol. 225:900, 1993); "Manipulating the Mouse Embryo: A laboratory manual" (Hogan et al., eds., Cold Spring Harbor Laboratory Press, 1994); and "Embryonic Stem Cells" (Turksen ed., Humana Press, 2002). The reagents and kits for cell culture and developmental and cell biological studies cited herein can be obtained from commercial sources including Invitrogen/GIBCO, Sigma and the like.

Standard protocols have also been established for preparing, subculturing and preserving mouse and human pluripotent stem cells, and in addition to the references cited above, the operator can use such pluripotent stem cells by consulting various other references. Such references include: Matsui et al., Cell 70:841, 1992; Thomson et al., U.S. Pat. No. 5,843,780; Thomson et al., Science 282:114, 1998; Shamblott et al., Proc. Natl. Acad. Sci. USA 95:13726, 1998; Shamblott et al., U.S. Pat. No. 6,090,622; Reubinoff et al., Nat. Biotech. 18:399, 2000; and International Publication No. WO00/27995. Methods for establishing ES cells or ES cell-like cells are also known for other animal species, e.g., monkeys (Thomson et al., U.S. Pat. No. 5,843,780; Proc. Natl. Acad. Sci. USA, 92, 7844, 1996), rats (Iannaccone et al., Dev. Biol. 163:288, 1994; Loring et al., International Publication No. WO99/27076), avians (Pain et al., Development 122:2339, 1996; U.S. Pat. No. 5,340,740; U.S. Pat. No. 5,656,479) and pigs (Wheeler et al., Reprod. Fertil. Dev. 6:563, 1994; Shim et al., Biol. Reprod. 57:1089, 1997). According to these described methods, ES cells for use in the present invention can be prepared and used.

In this disclosure, "cardiomyocytes" include cardiac precursor cells having the ability to become functional cardiomyocytes in the future, as well as fetal and adult cardiomyocytes at all stages of differentiation, and are defined as cells that can be identified by one or preferably more than one of the following methods using one or preferably more than one marker or index.

The expression of various markers specific to cardiomyocytes is detected by conventional biochemical or immunochemical methods. There is no particular limit on the method, but preferably an immunochemical method such as immunohistochemical staining or immunoelectrophoresis is used. In these methods, marker-specific polyclonal antibodies or monoclonal antibodies can be used which react with cardiac precursor cells or cardiomyocytes. Antibodies for individual specific markers are commercially available, and can be easily used. Markers specific to cardiac precursor cells or cardiomyocytes include for example myosin heavy and light chains, α-actinin, troponin I, ANP, GATA-4, Nkx2.5, MEF-2c and the like.

Alternatively, although the method is not particularly limited, expression of cardiac precursor cell-specific or cardiomyocyte-specific marker genes can also be confirmed by reverse transcriptase polymerase chain reaction (RT-PCR) or hybridization analysis, molecular biological methods which have been commonly used in the past for amplifying, detecting and analyzing mRNA encoding any marker proteins. The nucleic acid sequences encoding marker proteins specific to cardiac precursor cells and cardiomyocytes (such as myosin heavy and light chains, α-actinin, troponin I, ANP, GATA-4, Nkx2.5 and MEF-2c) are already known and are available through public databases such as GenBank of the National Center for Biotechnology Information (NCBI), and the marker-specific sequences needed for use as primers or probes can be easily determined.

Physiological indexes can also be used additionally to confirm differentiation of pluripotent cells into cardiomyocytes. For example, useful markers include spontaneous beating by cells derived from pluripotent cells, expression of various ion channels and the ability to react to electrophysiological stimulus.

The method of the present invention can be applied to pluripotent stem cells of any mammalian origin. For example, the method of the present invention can be used for pluripotent stem cells derived from mice, cows, goats, dogs, cats, marmosets, rhesus monkeys or humans, but is not limited to pluripotent stem cells derived from these animal species. Examples of pluripotent stem cells available for use in the present invention include ES cells derived from mammals such as mice, monkeys and humans, which are already widely used as cultured cells.

Specific examples of mouse-derived ES cells include EB3 cells, E14 cells, D3 cells, CCE cells, R1 cells, 129SV cells, J1 cells and the like. Mouse-derived ES cells for use in the present invention can be obtained from, e.g., American Type Culture Collection (ATCC), Chemicon, or Cell & Molecular Technologies.

Monkey-derived ES cells have been reported to be established from rhesus monkeys (*Macaca mulatta*) (Thomson et al., Proc. Natl. Acad. Sci. USA 92:7844, 1995), cynomolgus monkeys (*Macaca fascicularis*) (Suemori et al., Dev. Dyn. 222:273, 2001) and common marmosets (*Callithrix jacchus*) (Sasaki et al., Stem Cells. 23:1304, 2005), and can be used. For example, marmoset ES cells can also be obtained from the Central Institute for Experimental Animals, Japan.

At present, more than several tens of human-derived ES cell lines have been established all over the world. For example, many cell lines are registered in the list of the US National Institutes of Health (http://stemcells.nih.gov/registry/index.asp) and can be used, while these cell lines can also be purchased from, e.g., Cellartis, ES Cell International, or Wisconsin Alumni Research Foundation. In Japan, human ES cell lines can also be obtained from the Stem Cell Research Center, the Institute for Frontier Medical Sciences, Kyoto University (Suemori et al., Biochem. Biophys. Res. Commun., 345:926, 2006).

Moreover, establishment of ES cells has also been reported for cows (Mitalipova et al., Cloning 3:59, 2001), avians (Petitte et al., Mech. Dev. 121:1159, 2004) and zebrafish (Fishman, Science 294:1290, 2001).

Although ES cells are generally established by culturing early-stage embryos, ES cells can also be prepared from early-stage embryos which are modified to have somatic cell nuclei by nuclear transplantation (Munsie et al., Curr. Biol. 10:989, 2000; Wakayama et al., Science 292:740, 2001; Hwang et al., Science 303:1669, 2004). Moreover, there are reports about an attempt to prepare ES cells from parthenogenetic embryos which have been developed into a stage equivalent to the blastocyst stage (U.S. Patent Publication No. 02/168763; Vrana K et al., Proc. Natl. Acad. Sci. USA 100: 11911-6), as well as a method for preparing ES cells having the genetic information of somatic cell nuclei through fusion between ES cells and somatic cells (International Publication No. WO00/49137; Tada et al., Curr. Biol. 11:1553, 2001). ES cells for use in the present invention also include the ES cells thus prepared or ES cells whose chromosomal genes are modified by genetic engineering procedures.

Pluripotent stem cells available for use in the method of the present invention are not limited to ES cells, and also include all pluripotent stem cells characteristically similar to ES cells, which are derived from, e.g., mammalian adult organ or tissue cells, bone marrow cells and blood cells, as well as mammalian embryos or fetal cells. In this case, characteristical similarity to ES cells is defined in terms of cytobiological properties unique to ES cells, such as the presence of ES cell-specific surface markers (antigen), the expression of ES cell-specific genes, or the ability to produce teratomas or chimera mice. Specific examples include EG cells prepared from primordial germ cells, GS cells prepared from testicular germ cells, and induced pluripotent stem cells (iPS cells) prepared from somatic cells such as fibroblasts by particular gene manipulation.

Any method suited to inducing differentiation of cardiomyocytes can be used as the culture method for preparing cardiomyocytes from ES cells or other pluripotent stem cells in the present invention, and examples include suspension culture, hanging drop culture, co-culture with supporting cells, gyratory culture, soft agar culture, micro-carrier culture and the like. A specific example is a method of suspending ES cells as single cells (individual cells dispersed in a liquid phase with no adhesion between cells due to enzyme digestion or the like) in medium to a cell density of $1 \times 10^3$ to $1 \times 10^5$ cells/mL, and depositing a 10 to 100 µL droplet of the suspension onto the inner side of the upper dish of a culture plate to effect hanging drop culture. Alternatively, the above cell suspension may be seeded in a commercially available plate such as a 96-well culture plate for spheroid formation (e.g., Sumilon Celltight Spheroid; Sumitomo Bakelite Co., Ltd., Japan), a non-cell-adhesive culture plate (e.g., Coaster ultra-low-attachment plate; Corning) or an untreated polystyrene plate. The suspension containing ES cells is then cultured at 37° C. under $CO_2$ conditions with 5% carbon dioxide aeration, whereby EBs are formed and induced to differentiate into cardiomyocytes or other cells.

In the present invention, activation of the canonical Wnt signaling pathway means a state where β-catenin is not phosphorylated by GSK-3β and is stabilized within the cytoplasm and/or nucleus, and/or a state where β-catenin binds to LEF-1/TCF in the nucleus to form a transcription activator complex and thereby has the ability to induce transcription of a target gene. To determine whether the canonical Wnt signaling pathway is activated, any method may be used, including but not limited to a method for measuring the amount of cytoplasmic and/or nuclear β-catenin, e.g., by immunohistological staining with β-catenin-specific antibody or by Western blot analysis. Likewise, monoclonal antibodies which specifically recognize unphosphorylated β-catenin, i.e., active β-catenin are also commercially available and particularly useful. Moreover, reporter assays are also effective in which a reporter gene is linked downstream of a LEF-1/TCF binding sequence and the ability to produce the reporter gene product is used as a marker for assay. A plasmid containing a LEF-1/TCF binding sequence and a reporter gene for use in such assays can be purchased from Upstate under the trade name of TOPflash.

Specific examples of Wnt signaling activators include various canonical Wnt proteins, GSK-3β inhibitors and Wnt agonists. It is also possible to use genes capable of activating the canonical Wnt signaling pathway, e.g., various canonical Wnt genes, as well as β-catenin gene or active mutants thereof which are modified to delete the N-terminal end or to replace GSK-3β phosphorylation sites with unphosphorylated amino acids. Alternatively, expression of genes, such as Axin or APC, which downregulate the canonical Wnt signaling pathway may be suppressed or arrested by specific antisense DNAs or ribozymes, antisense RNAs for RNA interference, low molecular weight compounds and so on. It should be noted that the nucleotide sequences of genes encoding these molecules are available through public DNA databases such as those of NCBI, and those skilled in the art will be able to obtain, prepare and use cDNAs, siRNAs and/or antisense DNAs of these genes.

Canonical Wnt proteins available for use in the present invention are members of the Wnt family protein group and are defined as substances that bind to Fzd family receptors and inhibit GSK-3β-mediated phosphorylation of β-catenin to thereby promote stabilization of β-catenin and its transcription activation ability. Preferred canonical Wnt proteins in the present invention include, for example, Wnt-1 (SEQ ID NO: 1), Wnt-3a (SEQ ID NO: 2), Wnt-5a (SEQ ID NO: 3) and Wnt-8a (SEQ ID NO: 4), as well as those sharing an amino acid sequence homology of at least 80%, more preferably at least 90% with these proteins and having the ability to activate β-catenin.

One feature of the present invention is that ES cells or other pluripotent stem cells are transiently stimulated with a Wnt signaling activator, and while the stimulus method is not particularly limited, preferred is a method of culturing the cells in medium supplemented with a canonical Wnt protein, for example, a recombinant Wnt protein. However, any other method can be used which has the same effects. Examples include a method of culturing the cells in the presence of a canonical Wnt protein which has been extracted and purified from living tissues, a method of introducing an expression vector carrying a gene encoding a canonical Wnt protein into the pluripotent stem cells themselves, a method of introducing such an expression vector into supporting cells and using those transfected cells as co-culture cells, and a method using a culture supernatant or other cell product of those transfected cells and the like, all of which are included as part of the embodiment for adding a canonical Wnt protein to medium in the method of the present invention.

In implementing the present invention, a canonical Wnt protein to be used and a gene encoding the same are preferably derived from animals of the same species as that used to derive the pluripotent stem cells, but those derived from animals of another species can also be used. For example, when mouse ES cells or monkey ES cells are used in the present invention, it is possible to use human WNT-1 protein. As recombinant Wnt proteins, mouse-derived Wnt-3a and Wnt-5a as well as human-derived WNT-7A are commercially available from R&D Systems, and human-derived WNT-1 is commercially available from Peprotech. These recombinant Wnt proteins are easy to use. In the case of using these recombinant proteins, the culture medium is sterilely removed and replaced with fresh medium containing a Wnt protein at a concentration of 0.1 ng/mL to 500 ng/mL, preferably 1 ng/mL to 200 ng/mL, more preferably 10 ng/mL to 100 ng/mL, and culture is continued.

In a case where a desired Wnt protein is self made, it is necessary to introduce and express an expression vector carrying the gene of interest in animal cells (e.g., L cells) and to purify a recombinant protein secreted into the culture supernatant, because it is known that Wnt proteins do not exert their biological activity unless modified with palmitic acid. Detailed procedures for this purpose are already known (Willert et al., Nature 423:448, 2003; Kishida et al., Mol. Cell. Biol. 24:4487; http://www.stanford.edu/~rnusse/wntwindow.html).

It should be noted that the nucleotide sequences of genes encoding these factors are available through public DNA databases such as those of NCBI, and those skilled in the art will be able to obtain and use cDNAs of these genes. For example, Wnt-3a and Wnt-8a genes have already been identified in humans and mice, and the nucleotide sequences of human WNT-3A (SEQ ID NO: 5), mouse Wnt-3a (SEQ ID NO: 2), human WNT-8A (SEQ ID NO: 6) and mouse Wnt-8a (SEQ ID NO: 4) are registered under Accession Nos. NM_033131, NM_009522, NM_031933 and NM_009290, respectively.

GSK-3β inhibitors according to the present invention are defined as substances that inhibit the kinase activity of GSK-3β protein (e.g., the ability to phosphorylate (β-catenin); and more than several tens of inhibitors are already known (Martinez et al., Med. Res. Rev. 22:373, 2002; Meijer L et al., Trends Pharmacol. Sci. 25:471, 2004). Specific examples include lithium; valproic acid; benzazepinone family members Kenpaullone (9-bromo-7,12-dihydroindolo[3,2-d][1]benzazepin-6(5H)-one) and Alsterpaullone (9-nitro-7,12-dihydroindolo[3,2-d][1]benzazepin-6(5H)-one); indirubin derivatives 5-chloro-indirubin, indirubin-3'-monoxime and BIO (also called GSK-3β inhibitor IX; 6-bromoindirubin-3'-oxime); maleimide derivatives SB216763 (3-(2,4-dichlorophenyl)-4-(1-methyl-1H-indol-3-yl)-1H-pyrrole-2,5-dione) and SB415286 (3-[(3-chloro-4-hydroxyphenyl)amino]-4-(2-nitrophenyl)-1H-pyrrole-2,5-dione); thiadiazolidinone (TDZD) analogs TDZD-8 (also called GSK-3β inhibitor I; 4-benzyl-2-methyl-1,2,4-thiadiazolidine-3,5-dione) and OTDZT (also called GSK-3β inhibitor III; 2,4-dibenzyl-5oxothiadiazolidine-3-thione); a phenyl-α-bromomethylketone compound GSK-3β inhibitor VII (4-dibromoacetophenone); and a cell-permeable phosphorylated peptide L803-mts (also called GSK-3β peptide inhibitor; Myr-N-GKEAPPAPPQSpP-NH$_2$ (SEQ ID NO: 40)). These compounds are commercially available from Calbiochem or Biomol and are easy to use, but this is not a limitation.

In a case where these GSK-3β inhibitors are used, their optimum concentration will vary greatly depending on differences in their properties of compounds. For this reason, it is necessary to determine the optimum concentration of each compound to be used, and medium containing a GSK-3β inhibitor at a desired concentration is used for culture.

For example, in the case of BIO or SB216763, medium containing the inhibitor at a concentration of preferably 10 nmol/L to 1 µmol/L, more preferably 50 nmol/L to 200 nmol/L is used for culture. In the case of GSK-3β inhibitor VII, its concentration is preferably 2 µmol/L to 100 µmol/L, and more preferably 5 µmol/L to 20 µmol/L. Likewise, in the case of L803-mts, its concentration is preferably 5 µmol/L to 500 µmol/L, more preferably 20 µmol/L to 200 µmol/L, and even more preferably 25 µmol/L to 200 µmol/L.

In addition to GSK-3β inhibitors, drugs for use in implementing the present invention may be low molecular weight compounds that promote activation of the canonical Wnt signaling pathway (Wnt agonists), including organic or inorganic compounds and peptide fragments. Preferred examples include an aminopyrimidine derivative (2-amino-4-[3,4-(methylenedioxy)benzyl-amino]-6-(3-methoxyphenyl)pyrimidine; Calbiochem) (Liu et al., Angew. Chem. Int. Ed. Engl. 44:1987, 2005). In the case of using such a Wnt agonist, medium containing the Wnt agonist at a concentration of 1 nmol/L to 1000 nmol/L, preferably 10 nmol/L to 500 nmol/L, more preferably 50 nmol/L to 200 nmol/L is used for culture.

Determination of the timing at which pluripotent stem cells are treated with a Wnt signaling activator is a very important requirement in implementing the present invention. Namely, at an inappropriate timing, a Wnt signaling activator shows no promoting effect, or rather may have an inhibitory effect, on the myocardial differentiation ability of pluripotent stem cells. By way of example, when pluripotent stem cells are cultured for about 1 week in a culture medium supplemented with a Wnt signaling activator, starting from immediately after induction of differentiation, the myocardial differentiation ability may be lower than that observed in the group (untreated group) using a culture medium containing no additional ingredient.

The timing of Wnt signaling activator treatment can be determined based on the expression patterns of various canonical Wnt genes during induction of differentiation in pluripotent stem cells for use in implementing the present invention. More specifically, pluripotent stem cells may be induced to differentiate in a routine manner, and mRNAs may be extracted from the samples collected periodically to analyze the expression levels of various canonical Wnt genes by standard techniques such as RT-PCR. The samples are collected preferably every 24 hours, more preferably every 12 hours, during the time period between the initiation of culture for inducing differentiation and the appearance of (beating) cardiomyocytes, e.g., about 6 to 14 days for mouse, monkey and human ES cells. Although a single canonical Wnt gene may be used for analysis, preferably two or more, more preferably three or more genes are desired.

In ES cells and other pluripotent stem cells, expression of various canonical Wnt genes is generally low both in an undifferentiated state and immediately after induction of differentiation, but their expression is rapidly elevated several days after induction of differentiation (Example 1). In this way, a time point at which the expression levels of canonical Wnt genes are significantly elevated after induction of differentiation when compared to undifferentiated pluripotent stem cells is defined as the "period of elevated Wnt gene expression." Significant elevation in gene expression can be determined by commonly used statistical tests such as Student's t-test (significance level: 5%). The significance level used as a criterion in this case is preferably 5%, more preferably 1%. Alternatively, when the measured canonical Wnt gene expression is rapidly elevated within several days after induction of differentiation and then disappears within several days, i.e., when canonical Wnt genes show elevated expression only for a short period, a time point at which they reach maximum expression levels may be defined as the period of elevated Wnt gene expression.

When pluripotent stem cells are cultured in medium containing a BMP antagonist, starting from 2 or 3 days before induction of differentiation and/or starting from immediately after induction of differentiation, their myocardial differentiation ability is known to be significantly enhanced (WO2005/033298; Yuasa et al., Nat. Biotechnol. 23:607, 2005). In this case, the above various canonical Wnt genes were found to show elevated expression during culture. This finding is useful in determining the period of elevated canonical Wnt gene expression in the present invention, and it is desirable to use medium containing a BMP antagonist for culture in determining the period of elevated expression. A BMP antagonist refers to a substance that binds to a BMP molecule (e.g., BMP-2, BMP-4, BMP-7) to inhibit BMP signaling, and examples include Noggin, Chordin and DAN. These substances which may be added to medium can be purchased from, e.g., R&D systems.

In the present invention, pluripotent stem cells are cultured in medium containing no Wnt signaling activator during the time period between immediately after initiation of culture for inducing myocardial differentiation and 24 hours before the period of elevated Wnt gene expression determined as described above. Then, the cells are further cultured in medium containing a Wnt signaling activator for 24 to 96 hours, preferably for 48 to 72 hours, starting from a time point of 24 to 0 hours before, preferably 24 hours before the period of elevated Wnt gene expression determined as described above. For example, in one case of mouse ES cells cultured for inducing myocardial differentiation, expression of the typical canonical Wnt genes Wnt-3, Wnt-3a and Wnt-8a is extremely low both in an undifferentiated state and immediately after induction of differentiation, but these genes show strong expression between 72 and 96 hours after induction of differentiation (Example 1). For this reason, in a case where mouse ES cells are used in the method of the present invention, the period of elevated canonical Wnt gene expression is determined to be 72 hours after induction of differentiation, and hence the cells are cultured in medium containing no Wnt signaling activator until 48 hours after initiation of differentiation induction. Then, the cells are further cultured in medium containing a Wnt signaling activator for 24 to 96 hours, preferably for 48 to 72 hours, starting from 48 hours after initiation of differentiation induction. It should be noted that the time period (hours) during which the cells are treated with a Wnt signaling activator may be set to an optimum period (hours), as appropriate, depending on differences in conditions such as the species of animal from which cells to be used are derived, the type of cell line to be used, and/or the type of Wnt signaling activator to be used, and such a period (hours) can be determined based on the period of elevated canonical Wnt gene expression obtained by the above method for determining the timing of Wnt signaling activator treatment. For example, in the case of monkey (common marmoset) ES cells, the Wnt-3 gene shows strong expression between 72 and 120 hours after induction of differentiation (Example 5). Likewise, in the case of human ES cells, the Wnt-3a gene shows expression with a peak at around 72 hours after induction of differentiation (Beqqali et al., Stem Cells 24:1956, 2006).

Cardiomyocytes derived from ES cells or other pluripotent stem cells by the aforementioned method can be further collected, isolated and purified by known methods to efficiently obtain large quantities of highly pure cardiomyocytes (cardiomyocytes prepared according to the present invention).

Any known method of cell isolation and purification can be used as the method of purifying the cardiomyocytes, and specific examples include flow cytometry, magnetic beads, panning and other methods involving antigen-antibody reactions (see "Monoclonal Antibodies: principles and practice, Third Edition" (Acad. Press, 1993); "Antibody Engineering: A Practical Approach" (IRL Press at Oxford University Press, 1996) as well as cell fractioning by density gradient centrifugation using a carrier such as sucrose, Percoll or the like. Another method of selecting cardiomyocytes is to first artificially introduce a modification into the genes of the ES cells or other pluripotent stem cells, making them drug resistant or capable of ectopic protein expression, and collecting cells having the morphology of cardiomyocytes. For example, by introducing a gene cassette capable of expressing a neomycin (G418) resistance gene under the control of the α-myosin heavy chain promoter into mouse ES cells, Field and his co-researchers succeeded in constructing a system in which ES cells were differentiated into cardiomyocytes and only those cells which expressed the α-myosin heavy chain gene could survive in medium to which G418 had been added, and 99% or more of the cells selected as G418-resistant cells by this method were confirmed to be cardiomyocytes (U.S. Pat. No. 6,015,671; Klug et al., J. Clin. Invest. 98: 216, 1996). As another example, a method based on the higher mitochondrial content of cardiomyocytes than of other cells is also effective, in which mitochondria-rich cell populations, i.e., cardiomyocytes are specifically collected using a mitochondria-selective fluorescent dye or a mitochondrial membrane potential-sensitive reagent (WO2006/022377). As yet another example, a method based on specific metabolic properties of cardiomyocytes is also preferred, in which cardiomyocytes are specifically purified under low glucose conditions by addition of lactic acid or an amino acid such as aspartic acid (Japanese Patent Application No. 2006-23770).

Cardiomyocytes prepared according to the present invention are useful in pharmacological evaluations and activity evaluations of various bioactive substances (for example, drugs) and novel gene products of unknown function. For example, they can be used to screen for substances and drugs involved in controlling the differentiation of cardiomyocytes from ES cells and other pluripotent stem cells, for substances and drugs involved in regulating the function of cardiomyocytes, and for substances and drugs which are toxic or inhibitory towards cardiomyocytes. In particular, there are currently very few methods of screening using human cardiomyocytes, and the cardiomyocytes prepared according to the present invention provide a useful source of cells for implementing such screening methods. In another mode, an evaluation kit comprising cardiomyocytes prepared according to the present invention is also useful for such screening.

Test substances to be screened may include any which can be added to culture, such as low molecular weight compounds, high molecular weight compounds, organic compounds, inorganic compounds, proteins, peptides, genes, viruses, cells, cell culture fluids, microbial culture fluids and the like. Efficient methods of introducing genes into culture systems include methods of addition to culture systems using retroviruses, adenoviruses and other virus vectors as well as methods of addition after insertion into liposomes and other artificial constructs.

The test substance can be evaluated by measuring the efficiency of induction of differentiation from ES cells or other pluripotent stem cells into cardiomyocytes, or the qualitative or quantitative changes in myocardial cell functions. For example, the myocardial differentiation induction efficiency of a test substance can be measured by using biochemical or immunochemical means to detect the expression of various cardiomyocyte-specific markers in pluripotent stem cells cultured using the method of the present invention after they have been cultured for 5 to 15 or preferably 7 to 12 days. There are no particular limits on the biochemical or immunochemical means, but preferably an immunochemical method such as immunohistochemical staining or immunoelectrophoresis can be used. Marker-specific polyclonal antibodies or monoclonal antibodies that bind to the cardiomyocytes can be used in these methods. Antibodies that target individual specific markers are commercially available and can be easily used. Examples of cardiomyocyte-specific markers include myosin heavy and light chains, α-actinin, troponin I, ANP, GATA-4, Nkx2.5, MEF-2c and the like.

Myocardial cell survival is one example of a myocardial cell function that can be used as a marker for evaluating a test substance. Specifically, cell death (apoptosis) can be induced by seeding cardiomyocytes prepared by the method according to the present invention on a culture plate to an appropriate cell density and culturing them in serum-free medium, and in this case a suitable amount of the test substance can be added to the medium and the survival rate or death rate of cardiomyocytes can be measured. The survival rate or death rate of the cardiomyocytes can be measured by macroscopic observation using incorporation of a dye such as trypan blue as the marker, by a method using dehydrogenase activity (reduction activity) as the marker, or by a method using annexin V expression or caspase activity, which are specific to apoptosis cells, as the marker. Kits exploiting these mechanisms are available from many manufacturers including Sigma, Clonetech and Promega, and are easy to use.

Because a substance or drug obtained by such a screening method acts to induce differentiation of cardiomyocytes and regulate their functions, it can be used for example as a preventative or therapeutic drug for heart conditions including myocardial infarction, ischemic heart disease, congestive heart failure, hypertrophic cardiomyopathy, dilative cardiomyopathy, myocarditis, chronic heart failure and the like. These compounds may be novel compounds or known compounds.

Moreover, cardiomyocytes prepared according to the present invention can be used as myocardial regeneration drugs or heart disease treatment drugs. Examples of heart disease include myocardial infarction, ischemic heart disease, congestive heart failure, hypertrophic cardiomyopathy, dilative cardiomyopathy, myocarditis, chronic heart failure and the like. When used as myocardial regeneration drugs or heart disease treatment drugs, cardiomyocytes prepared according to the present invention can be included in any form as long as the purity is high, such as cells suspended in the medium or other aqueous carrier, cells embedded in a biodegradable substrate or other support, or cells made into a single-layer or multilayer myocardial sheet (Shimizu et al., Circ. Res. 90:e40, 2002).

Although not particularly limited to these, methods for transporting the aforementioned therapeutic drug to a damage site include direct injection into the heart via an open chest or syringe, methods of transplantation via a surgical incision in the heart, and methods of transplantation via the blood vessels using a catheter (Murry et al., Cold Spring Harb. Symp. Quant. Biol. 67:519, 2002; Menasche, Ann. Thorac. Surg. 75:S20, 2003; Dowell et al., Cardiovasc. Res. 58:336, 2003). Extremely good therapeutic effects have been reported when cardiomyocytes collected from a fetal heart were transplanted by such methods to the hearts of animals with heart damage (Menasche, Ann. Thorac. Surg. 75:S20, 2003; Reffelmann et al., Heart Fail. Rev. 8:201, 2003). Cardiomyocytes derived from ES cells have characteristics extremely similar to those of cardiomyocytes derived from fetal hearts (Maltsev et al., Mech. Dev. 44:41, 1993; Circ. Res. 75:233, 1994; Doevendans et al., J. Mol. Cell. Cardiol. 32:839, 2000). Moreover, an extremely high take rate equivalent to that achieved with fetal myocardial transplantation has been confirmed in animal experiments in which cardiomyocytes derived from ES cells were actually transplanted into adult hearts (Klug et al., J. Clin. Invest. 98:216, 1996; Laflamme et al., Am. J. Pathol. 167:663). Consequently, it is expected that supplementary transplantation of cardiomyocytes prepared according to the present invention into diseased heart tissue should stimulate improved heart functions in cases of the aforementioned heart diseases stemming from damage or loss of heart cells.

EXAMPLES

The present invention is explained in more detail below using examples.

Example 1

Study on Expression Patterns of Various Wnt Genes During Induction of Differentiation in ES Cells (1)

Various Wnt genes were studied for their expression during differentiation in mouse ES cells. For use in experiments, mouse ES cells were passaged and maintained in an undifferentiated state according to the methods as described in "Manipulating the Mouse Embryo: A Laboratory Manual" (Hogan et al., eds., Cold Spring Harbor Laboratory Press, 1994) and "Embryonic Stem Cells: Methods and Protocols" (Turksen ed., Humana Press, 2002) by using Knockout-DMEM (Invitrogen) medium containing 20% fetal bovine serum, 2 mmol/L L-glutamine and 0.1 mmol/L 2-mercaptoethanol (hereinafter referred to as ESM), supplemented with 1000 U/mL LIF (ESGRO; Chemicon). ES cells passaged under these conditions are hereinafter referred to as "ES cells passaged under ordinary culture conditions." The mouse ES cells used in the following experiments were D3 cells, R1 cells and 129SV cells (purchased from Dainippon Pharmaceutical Co., Ltd., Japan), but in general there were no differences in the experimental results between these ES cell lines. Unless otherwise indicated, experimental data obtained with the D3 cell line are shown below. It should be noted that mouse ES cells were used in the experiments of Examples 1 to 4.

ES cells passaged under ordinary culture conditions were washed twice with phosphate-buffered saline (hereinafter referred to as PBS) and treated with 0.25% trypsin solution containing 1 mmol/L EDTA to obtain single cells, which were then suspended in ESM. Unless otherwise indicated, the same conditions were used in detaching the ES cells from plates for use in induction of differentiation and other experiments.

Culture for inducing differentiation of ES cells into cardiomyocytes or neurons was accomplished in a routine manner as follows. ES cells were suspended in LIF-free medium, and the resulting suspension was seeded at 500 cells/50 µL per well of a commercially available 96-well culture plate for spheroid formation (Sumilon Celltight Spheroid; Sumitomo Bakelite Co., Ltd., Japan). Under these experimental conditions, the ES cells began to aggregate and form EBs immediately after suspension culture, and some EBs began to exhibit spontaneous beating about 7 or 8 days after floating aggregation culture (induction of differentiation), indicating that at least part of the EBs differentiated into cardiomyocytes.

In this experiment, some of the experimental groups received addition of a commercially available recombinant Chordin or DAN protein (15 ng/mL; both purchased from R&D systems) to the medium at 3 days before and immediately after induction of differentiation. When transiently treated with a BMP antagonist in this way, ES cells are known to enhance their myocardial differentiation ability (WO2005-033298; Yuasa et al., Nat. Biotechnol. 23:607, 2005). Treatment of ES cells in medium supplemented with a BMP antagonist such as Chordin protein or DAN protein is hereinafter referred to as "BMP antagonist treatment."

The EBs thus prepared were collected periodically, and total RNA was prepared with an RNeasy mini kit (Qiagen), followed by DNase treatment. cDNA was synthesized from the DNase-treated total RNA (1 µg) using a SuperScript™ First-Strand Synthesis System for RT-PCR (Invitrogen). Analysis of gene expression was performed with an ABI PRISM 7700 (PE Applied Biosystems) by using a real-time polymerase chain reaction (PCR) quantification system with Lux primers to examine the expression level of each gene. The real-time PCR quantification was accomplished by using the above cDNA as a template and using Platinum Quantitative PCR SuperMix-UDG (Invitrogen) according to the instructions attached thereto.

Lux primers for detection of various Wnt genes were designed using primer design software (D-LUX™ Designer; Invitrogen) on the basis of the nucleotide sequence information of the genes. The nucleotide sequences of the Lux primers used for detection of various Wnt gene transcripts are as shown below.

```
Wnt-3
(Forward)                               (SEQ ID NO: 7)
5'-CAACAGTAGCAAGGAGCATGGACTGTTG-3'

(Reverse)                               (SEQ ID NO: 8)
5'-GGCTGGGTCCAGGTCGTTTA-3'

Wnt-3a
(Forward)                               (SEQ ID NO: 9)
5'-GACAAACCGGGAGTCAGCCTTTGTC-3'

(Reverse)                               (SEQ ID NO: 10)
5'-TGCTGCACCCACAGATAGCA-3'

Wnt-8a
(Reverse)                               (SEQ ID NO: 11)
5'-GTACATGCGCTCTGCTGCCATCATGTAC-3'

(Forward)                               (SEQ ID NO: 12)
5'-GACTCGTCACAGCCGCAGTT-3'
```

FIG. 1 shows one example of the experiments performed as described above. The Wnt genes were examined for their expression between 24 hours (1 day) and 168 hours (7 days) after induction of differentiation in ES cells, indicating that Wnt-3, Wnt-3a and Wnt-8a genes showed significant elevations in their expression. These Wnt genes each showed a peak of strong expression between 72 and 96 hours after induction of differentiation, and their expression was then significantly decreased from 120 hours after induction of differentiation. Thus, in theses ES cells, the period of elevated Wnt gene expression can be determined to be 72 hours after induction of differentiation.

The groups treated with a BMP antagonist such as Chordin protein or DAN protein showed strong elevations in Wnt genes expression at 72 hours after induction of differentiation, as in the case of the untreated group, and the expression levels of the Wnt genes were found to be significantly higher than those of the untreated group. These results indicate that BMP antagonist treatment is a method capable of more precisely determining the period of elevated Wnt gene expression during ES cell differentiation.

Example 2

Enhancing Effect of Recombinant Wnt Protein Treatment on the Appearance of Cardiomyocytes Derived from ES Cells (1)

In the early stage of differentiation in ES cells, transient elevations in expression of various Wnt genes were observed prior to the appearance of cardiomyocytes. Then, ES cells at this stage were treated with recombinant Wnt proteins to study the myocardial differentiation-inducing effect of the proteins. Induction of ES cell differentiation was accomplished in the same manner as used in Example 1, except that some of the experimental groups were cultured in medium containing a commercially available recombinant WNT-1 (Peprotech), Wnt-3a (R&D systems) or Wnt-5a (R&D systems) protein. Treatment of ES cells in medium supplemented with a recombinant protein of canonical Wnt such as WNT-1 is hereinafter referred to as "Wnt treatment."

The appearance rate of EBs exhibiting spontaneous beating was investigated periodically as one of a useful index of the differentiation and development of cardiomyocytes from ES cells. In the untreated group, the appearance rate of beating EBs was around 20% at 13 days after suspension culture, whereas in the group receiving Wnt treatment for 48 hours (2 days) between 48 and 96 hours after induction of differentiation ($Wnt^{48 \sim 96h}$) as well as the group receiving Wnt treatment for 72 hours (3 days) between 48 and 120 hours after induction of differentiation ($Wnt^{48 \sim 120h}$), beating was observed in a significantly high percentage of EBs (FIGS. 2A and 2B). The effect of Wnt treatment was as high as comparable to that of BMP antagonist treatment ("Chordin" in the figure).

In contrast, in the group receiving Wnt treatment for the first 48, 72, 96 or 120 hours (2, 3, 4 or 5 days) after induction of differentiation ($Wnt^{-48h}$, $Wnt^{-72h}$, $Wnt^{-96h}$ or $Wnt^{-120h}$, respectively) as well as the group receiving Wnt treatment from 120 or 144 hours (5 or 6 days) after induction of differentiation ($Wnt^{120h\sim}$ or $Wnt^{144h\sim}$), EBs with beating ability appeared at the same level as in the untreated group. Moreover, in EBs from the untreated group and other groups with a low percentage of beating EBs, beating was limited to a certain restricted regions of the EBs, whereas EBs from the $Wnt^{48 \sim 96h}$ and $Wnt^{48 \sim 120h}$ groups were found to exhibit beating throughout virtually all regions of their surface layer, as in the case of Chordin-treated EBs. Namely, even when ES cells were cultured in medium containing a Wnt protein during the time period between immediately after induction of differentiation and 24 hours before the period showing elevated Wnt gene expression (i.e., 72 hours after initiation of differentiation induction), there was no significant effect on induction of myocardial differentiation.

In contrast, when ES cells were cultured in medium containing a recombinant Wnt protein for 48 hours (2 days) or 72 hours (3 days) starting from 24 hours before the period showing elevated Wnt gene expression (i.e., 72 hours after initiation of differentiation induction), there was a significant enhancing effect on myocardial differentiation ability.

These results indicated that although Wnt treatment significantly induced myocardial differentiation from ES cells, its effect was observed only for a very limited period during induction of differentiation. In the following experiments, the term "Wnt treatment" is used to mean Wnt treatment for 48 hours (2 days) between 48 and 96 hours after initiation of differentiation induction or for 72 hours (3 days) between 48 and 120 hours after initiation of differentiation induction, unless otherwise indicated.

Further studies were performed on "Wnt treatment" to investigate how differences in the concentration of added recombinant Wnt proteins would affect the ability of myocardial differentiation. By way of example, in the case of using Wnt-3a, Wnt-5a and WNT-1, they showed almost the same concentration dependency, and the appearance rate of beating EBs was significantly higher than in the untreated group when the recombinant proteins were added at concentrations of 1 ng/mL to 100 ng/mL. In particular, a very good occurrence of beating EBs was obtained through addition of the Wnt proteins at concentrations of 10 ng/mL to 50 ng/mL.

Example 3

Properties of Cardiomyocytes Derived from Wnt-Treated ES Cells

As shown in Example 2, beating of EBs prepared from ES cells was increased significantly by Wnt treatment, and to confirm that the beating cells in these EBs were cardiomyocytes, further studies were performed to investigate gene expression and protein production of various myocardial-specific marker molecules. In the same manner as used in Example 2, ES cells were induced to differentiate and the resulting EBs were collected at 10 days after induction of differentiation to prepare cDNA. Real-time PCR quantification was performed by the TaqMan probe method, i.e., by using the above cDNA (1 μL) as a template and using a TaqMan Universal PCR Master Mix (PE Applied Biosystems) according to the instructions attached thereto. TaqMan probes for detection of various genes were designed using primer design software (ABI PRISM Primer Express) on the basis of the nucleotide sequence information of the genes. The nucleotide sequences of the primers and TaqMan probes used for detection of GATA-4, Nkx-2.5, MLC-2a, MLC-2v and GAPDH transcripts are as shown below.

```
GATA-4
(Forward)                               (SEQ ID NO: 13)
5'-ACGGAAGCCCAAGAACCTGA-3', (Reverse)                               (SEQ ID NO: 14)
5'-CATTGCTGGAGTTACCGCTG-3', (TaqMan probe)                          (SEQ ID NO: 15)
5'-TAAATCTAA GACGCCAGCAGGTCCTGCTG-3';

Nkx-2.5
(Forward)                               (SEQ ID NO: 16)
5'TGACCCAGCCAAAGACCCT-3', (Reverse)                               (SEQ ID NO: 17)
5'-CCATCCGTCTCGGCTTTGT-3', (TaqMan probe)                          (SEQ ID NO: 18)
5'-CGGATAAAAAAGA GCTGTGCGCGC-3';

MLC-2a
(Forward)                               (SEQ ID NO: 19)
5'-CCAGGCAGACAAGTTCTCTCCT-3', (Reverse)                               (SEQ ID NO: 20)
5'-CTTGTAGTCAATGTTGCCGGC-3', (TaqMan probe)                          (SEQ ID NO: 21)
5'-CAACTGTTTGCGCTGACACCCATGGA-3';
```

```
MLC-2v
(Forward)                              (SEQ ID NO: 22)
5'-GCAGAGAGGTTCTCCAAAGAGG-3', (Reverse)                              (SEQ ID NO: 23)
5'-AAGATTGCCGGTAACGTCAGG-3', (TaqMan probe)                         (SEQ ID NO: 24)
5'-ATCGACCAGATGTTCGCAGCCTTTCC-3'

GAPDH
(Forward)                              (SEQ ID NO: 25)
5'-TGCACCACCAACTGCTTAG-3', (Reverse)                              (SEQ ID NO: 26)
5'-GGATGCAGGGATGATGTTC-3', (TaqMan probe)                         (SEQ ID NO: 27)
5'-CAGAAGACTGTG GATGGCCCCTC-3'
```

When compared to the untreated group, EBs in the Wnt-treated group ($Wnt^{48\sim120h}$ group) at 10 days after induction of differentiation showed significantly stronger expression for GATA-4, Nkx-2.5, MLC-2a and MLC-2v genes (FIG. 3) as well as αMHC and βMHC genes, each of which genes is known as a typical cardiomyocyte marker.

In contrast, in the $Wnt^{\sim48h}$, $Wnt^{\sim120h}$ and $Wnt^{144h\sim}$ groups showing a low appearance rate of beating EBs, the expression levels of the marker genes were almost the same as in the untreated group, and substantially the same tendencies were observed for the appearance rate of beating EBs and the expression levels of various myocardial marker genes.

Subsequently, immunohistochemical staining was performed to confirm that beating cells developed in EBs from the Wnt-treated groups produced cardiomyocyte-specific marker proteins. EBs in the Wnt-treated group ($Wnt^{48\sim120h}$ group) at 10 days after induction of differentiation were freshly embedded in a compound for preparing frozen sections (OCT Compound, Sakura Finetek USA Inc.) and then frozen with liquid nitrogen. The frozen samples were sectioned at 6 μm of thickness and attached on glass slides. These frozen sections were reacted with anti-sarcomeric myosin antibody (MF20; American Type Culture Collection), anti-GATA-4 antibody (C-20; Santa Cruz) or anti-Nkx-2.5 antibody (N-19; Santa Cruz) as a primary antibody and then reacted with a horseradish peroxidase-labeled secondary antibody (Bio-RAD), and finally subjected to a color reaction with ACE (3-amino-9-ethylcarbazole) substrate solution (Nichirei Corporation, Japan) and observed under an optical microscope.

The results obtained are shown in FIG. 4. In the untreated group, cells positive for cardiomyocyte-specific marker proteins sarcomeric myosin ("MHC" in the figure), Nkx-2.5 and GATA-4 were observed in a very limited number of EBs. In contrast, in the Wnt-treated group, the great majority of EB-constituting cells were found to be positive for the marker proteins and were confirmed to form cardiospheres, as in the case of the BMP antagonist (DAN)-treated group. These results proved that beating cells derived from Wnt-treated ES cells were cardiomyocytes, and also indicated that this method strongly promoted cardiomyocyte differentiation and development in EBs.

Example 4

Enhancing Effect of β-Catenin Activator on the Appearance of Cardiomyocytes Derived from ES Cells The above canonical Wnt protein treatment is known to inhibit the action of GSK3β within cells and thereby promote stabilization of β-catenin and its transcription activation ability. Then, further studies were performed to confirm that treatment with various drugs capable of promoting stabilization of β-catenin and its transcription activation ability produced a myocardial differentiation-inducing effect on ES cells, as in the case of Wnt treatment. As drugs capable of promoting stabilization of β-catenin and its transcription activation ability, the following five commercially available compounds were used: GSK3β inhibitors BIO (Calbiochem), GSK3β inhibitor VII (Calbiochem), cell-permeable GSK3β peptide inhibitor (L803-mts; Calbiochem) and SB216763 (Biomol), as well as a Wnt agonist (Calbiochem) that promotes the transcription activation ability of β-catenin without GSK3β inhibition. ES cells were induced to differentiate in the same manner as used in the above Examples, and cultured in medium containing the above compounds during the time period between 48 and 120 hours (3 and 5 days) after induction of differentiation, as in the case of recombinant Wnt proteins.

As shown in FIG. 5, the results confirmed that the groups treated with the above compounds showed, at their optimum concentrations, a strong myocardial differentiation-inducing effect comparable to or greater than that of the recombinant Wnt protein-treated groups. In the same manner as used in Example 3, EBs treated with these compounds were studied for their expression of myocardial marker genes and myocardial marker proteins, indicating that they showed a significantly higher elevating effect on gene and protein expression than the untreated group, as in the case of the recombinant Wnt protein-treated groups.

Example 5

Study on Expression Patterns of Wnt Genes During Induction of Differentiation in ES Cells (2)

ES cells derived from common marmoset, a kind of monkey (hereinafter referred to as "cmES cells") were used to study Wnt gene expression during their differentiation. For use in experiments, cmES cells were passaged and maintained in an undifferentiated state on mitomycin-treated primary mouse embryonic fibroblasts which had been seeded as feeder cells, by using Knockout-DMEM medium (Invitrogen) containing 20% Knockout Serum Replacement (Invitrogen), 0.1 mmol/L MEM nonessential amino acid solution, 1 mmol/L L-glutamine and 0.1 mmol/L 2-mercaptoethanol (hereinafter referred to as "cmES medium"), supplemented with 10 ng/mL recombinant LIF (alomone labs) and 10 ng/mL recombinant basic fibroblast growth factor (Invitrogen).

Culture for inducing differentiation in cmES cells was accomplished in a routine manner as follows. cmES cells were washed with PBS and then treated with a commercially available cell dissociation solution for primate ES cells (ReproCELL) at 37° C. for 5 minutes to collect a cell suspension containing cmES cell aggregates. Next, to separate the cmES cells from the feeder cells, the cell suspension was passed through a mesh of 100 μm pore size and the passed cell fraction was then passed through a mesh of 40 μm pore size to collect the non-passed fraction remaining on the mesh. This non-passed fraction containing cmES cell aggregates was further seeded in a commercially available culture plate with high cell attachment (Primaria; Becton Dickinson) and cultured for 30 minutes, followed by collection of cell aggregates floating in the medium without adhering to the plate. The cmES cell aggregates thus obtained were induced to differentiate into EBs by culturing in a commercially available non-cell-adhesive culture plate (HydroCell; CellSeed) filled with cmES medium while preventing cell aggregates from contacting with and adhering to each other.

The EBs thus prepared were collected periodically, and total RNA was prepared with an RNeasy mini kit (Qiagen). cDNA was then synthesized with reverse transcriptase and analyzed by PCR to detect expression of common marmoset Wnt-3 gene (cmWnt-3) and β-actin (cmβActin) serving as an endogenous control. The primers used for detection are as shown below.

```
cmWnt-3
(Forward)                       (SEQ ID NO: 28)
5'-GAGGTGAAGACCTGCTGGTGGGC-3'

(Reverse)                       (SEQ ID NO: 29)
5'-GTTGGGCTCACAAAAGTTGG-3' cmβActin
(Forward)                       (SEQ ID NO: 30)
5'-TCCTGACCCTGAAGTACCCC-3'

(Reverse)                       (SEQ ID NO: 31)
5'-GTGGTGGTGAAGCTGTAGCC-3'
```

FIG. 6 shows one example of the experiments performed as described above. The genes were examined for their expression between 24 hours (1 day) and 168 hours (7 days) after induction of differentiation in cmES cells, indicating that the Wnt-3 gene showed a peak of strong expression between 72 and 120 hours after induction of differentiation, and then its expression disappeared (FIG. 6). Thus, in these ES cells, the period of elevated Wnt-3 gene expression can be determined to be 72 hours after induction of differentiation, thereby obtaining almost the same results as in mouse ES cells.

Example 6

Enhancing Effect of Recombinant Wnt Protein Treatment on the Appearance of Cardiomyocytes Derived from ES Cells (2)

cmES cells were used to study the effect of recombinant Wnt protein treatment. In the same manner as used in Example 5, cmES cells were cultured and induced to differentiate. In this case, some of the experimental groups were cultured for 72 hours (3 days) between 48 and 120 hours after induction of differentiation in medium containing a commercially available recombinant WNT-1 (PeproTech), Wnt-3a (R&D systems) or WNT-7A (R&D systems) protein.

To confirm differentiation and development of cardiomyocytes from the cmES cells, the resulting EBs were observed for their spontaneous beating ability and also investigated for gene and protein expression of various myocardial-specific marker molecules. In the untreated group, 10% or less of EBs exhibited partial beating about 2 weeks after induction of differentiation. In contrast, in the Wnt-treated groups, spontaneous beating started about 10 days after induction of differentiation, and almost half of EBs exhibited beating at 16 days after induction of differentiation.

Moreover, for analysis of expressed genes, EBs were collected at 10 days after induction of differentiation to detect expression of various marker genes in the same manner as used in Example 5. The primers used for detection of common marmoset Nestin, ANP, MLC-2a and MLC-2v transcripts (hereinafter referred to as cmNestin, cmANP, cmMLC-2a and cmMLC-2v, respectively) are as shown below.

```
cmNestin
(Forward)                       (SEQ ID NO: 32)
5'-GCCCTGACCACTCCAGTTTA-3', (Reverse)                       (SEQ ID NO: 33)
5'GGAGTCCTGGATTTCCTTCC-3'

CmANP
(Forward)                       (SEQ ID NO: 34)
5'-GAACCAGAGGGGAGAGACAGA-3', (Reverse)                       (SEQ ID NO: 35)
5'-CCCTCAGCTTGCTTTTTAGGAG-3' cmMLC-2a
(Forward)                       (SEQ ID NO: 36)
5'-GAGGAGAATGGCCAGCAGGAA-3', (Reverse)                       (SEQ ID NO: 37)
5'-GCGAACATCTGCTCCACCTCA-3' cmMLC-2v
(Forward)                       (SEQ ID NO: 38)
5'-AGGAGGCCTTCACTATCATGG-3', (Reverse)                       (SEQ ID NO: 39)
5'-GTGATGATGTGCACCAGGTTC-3'
```

When compared to the untreated group, EBs in the Wnt-3a-treated group at 10 days after induction of differentiation showed significantly stronger expression for the typical cardiomyocyte marker genes cmANP, cmMLC-2a and cmMLC-2v (FIG. 7). Similar results were also obtained for EBs in the WNT-1-treated group.

In contrast, expression of cmNestin known as a neuronal marker was significantly reduced in the Wnt-treated groups.

Subsequently, immunohistochemical staining was performed in the same manner as used in Example 2 to confirm that beating cells developed in EBs from the Wnt-treated groups were cardiomyocytes producing specific marker proteins. From EBs in the Wnt-treated groups (Wnt-3a, WNT-1) at 16 days after induction of differentiation, frozen sections were prepared and reacted with anti-sarcomeric myosin antibody, anti-GATA-4 antibody or anti-Nkx-2.5 antibody as a primary antibody. After color reaction, these sections were observed under an optical microscope.

As a result, in the untreated group, cells positive for cardiomyocyte-specific marker proteins sarcomeric myosin and GATA-4 were observed in a very limited number of EBs, and there were little cells positive for Nkx-2.5. In contrast, in the groups treated with Wnt-3a or WNT-1, the great majority of EB-constituting cells were found to be positive for these marker proteins (FIG. 8). Similar results were also obtained for EBs in the WNT-7A-treated group.

These results indicated that Wnt treatment had a significant promoting effect on induction of myocardial differentiation not only in rodent ES cells but also in primate ES cells.

The invention claimed is:

1. A method for inducing differentiation of cardiomyocytes from mammalian pluripotent stem cells, which comprises:
   i) culturing the mammalian pluripotent stem cells in a culture medium containing no substance that promotes activation of the canonical Wnt signaling pathway during the time period between initiation of differentiation induction and 24 hours before the period of elevated canonical Wnt gene expression; and then
   ii) culturing the mammalian pluripotent stem cells in a culture medium containing a substance that promotes activation of the canonical Wnt signaling pathway during a time period of 24 to 96 hours, starting from 24 to 0 hours before the period of elevated canonical Wnt gene expression, wherein the substance that promotes activation of the canonical Wnt signaling pathway is a substance selected from the group consisting of a canonical Wnt protein, a GSK3β inhibitor, and a Wnt agonist.

2. The method according to claim 1, wherein the mammalian pluripotent stern cells are cultured in a culture medium containing a substance that promotes activation of the canonical Wnt signaling pathway, starting from 24 hours before the period of elevated canonical Wnt gene expression.

3. The method according to claim 1, wherein the mammalian pluripotent stem cells are cultured in a culture medium containing a substance that promotes activation of the canonical Wnt signaling pathway during a time period of 48 to 72 hours.

4. The method according to claim 1, wherein the substance that promotes activation of the canonical Wnt signaling pathway is a canonical Wnt protein.

5. The method according to claim 4, wherein the canonical Wnt protein is at least one Wnt protein selected from the group consisting of Wnt-1, Wnt-3a and Wnt-5a.

6. The method according to claim 4, wherein the concentration of the canonical Wnt protein in the culture medium is 0.1 ng/ml, to 500 ng/mL.

7. The method according to claim 1, wherein the substance that promotes activation of the canonical Wnt signaling pathway is a GSK3β inhibitor.

8. The method according to claim 7, wherein the GSK3β inhibitor is at least one inhibitor selected from the group consisting of GSK3β inhibitor VII, L803-mts, SB216763 and GSK3β inhibitor IX (BIO).

9. The method according to claim 7, wherein the concentration of the GSK3β inhibitor in the culture medium is 2 μmol/L to 100 μmol/L for GSK3β inhibitor VII, 5 μmol/L to 500 μmol/L for L803-mts, 10 nmol/L to 1 μmol/L for SB216763, or 10 nmol/L to 1 μmol/L for GSK3β inhibitor IX (BIO).

10. The method according to claim 1, wherein the substance that promotes activation of the canonical Wnt signaling pathway is a Wnt agonist.

11. The method according to claim 10, wherein the Wnt agonist is 2-amino-4-[3,4-(methylenedioxy)benzyl-amino]-6-(3-methoxyphenyl)-primidine.

12. The method according to claim 10, wherein the concentration of the Wnt agonist in the culture medium is 1 nmol/L to 1000 nmol/L.

13. The method according to claim 1, wherein the mammalian pluripotent stem cells are mammalian embryonic stem cells, mammalian embryonic germ cells or mammalian germline stem cells.

14. The method according to claim 13, wherein the mammalian pluripotent stem cells are mammalian embryonic stem cells.

15. The method according to claim 13, wherein the mammalian pluripotent stem cells are of human origin.

* * * * *

```
                          SEQUENCE LISTING

<160> NUMBER OF SEQ ID NOS: 40

<210> SEQ ID NO 1
<211> LENGTH: 370
<212> TYPE: PRT
<213> ORGANISM: Mus musculus

<400> SEQUENCE: 1

Met Gly Leu Trp Ala Leu Leu Pro Ser Trp Val Ser Thr Thr Leu Leu
1               5                   10                  15

Leu Ala Leu Thr Ala Leu Pro Ala Ala Leu Ala Ala Asn Ser Ser Gly
                20                  25                  30

Arg Trp Trp Gly Ile Val Asn Ile Ala Ser Ser Thr Asn Leu Leu Thr
            35                  40                  45

Asp Ser Lys Ser Leu Gln Leu Val Leu Glu Pro Ser Leu Gln Leu Leu
    50                  55                  60

Ser Arg Lys Gln Arg Arg Leu Ile Arg Gln Asn Pro Gly Ile Leu His
65                  70                  75                  80

Ser Val Ser Gly Gly Leu Gln Ser Ala Val Arg Glu Cys Lys Trp Gln
                85                  90                  95

Phe Arg Asn Arg Arg Trp Asn Cys Pro Thr Ala Pro Gly Pro His Leu
            100                 105                 110

Phe Gly Lys Ile Val Asn Arg Gly Cys Arg Glu Thr Ala Phe Ile Phe
        115                 120                 125

Ala Ile Thr Ser Ala Gly Val Thr His Ser Val Ala Arg Ser Cys Ser
    130                 135                 140

Glu Gly Ser Ile Glu Ser Cys Thr Cys Asp Tyr Arg Arg Arg Gly Pro
145                 150                 155                 160

Gly Gly Pro Asp Trp His Trp Gly Gly Cys Ser Asp Asn Ile Asp Phe
                165                 170                 175

Gly Arg Leu Phe Gly Arg Glu Phe Val Asp Ser Gly Glu Lys Gly Arg
            180                 185                 190

Asp Leu Arg Phe Leu Met Asn Leu His Asn Asn Glu Ala Gly Arg Thr
        195                 200                 205

Thr Val Phe Ser Glu Met Arg Gln Glu Cys Lys Cys His Gly Met Ser
    210                 215                 220

Gly Ser Cys Thr Val Arg Thr Cys Trp Met Arg Leu Pro Thr Leu Arg
225                 230                 235                 240

Ala Val Gly Asp Val Leu Arg Asp Arg Phe Asp Gly Ala Ser Arg Val
                245                 250                 255

Leu Tyr Gly Asn Arg Gly Ser Asn Arg Ala Ser Arg Ala Glu Leu Leu
            260                 265                 270

Arg Leu Glu Pro Glu Asp Pro Ala His Lys Pro Pro Ser Pro His Asp
        275                 280                 285

Leu Val Tyr Phe Glu Lys Ser Pro Asn Phe Cys Thr Tyr Ser Gly Arg
    290                 295                 300

Leu Gly Thr Ala Gly Thr Ala Gly Arg Ala Cys Asn Ser Ser Ser Pro
305                 310                 315                 320

Ala Leu Asp Gly Cys Glu Leu Leu Cys Cys Gly Arg Gly His Arg Thr
                325                 330                 335

Arg Thr Gln Arg Val Thr Glu Arg Cys Asn Cys Thr Phe His Trp Cys
            340                 345                 350

Cys His Val Ser Cys Arg Asn Cys Thr His Thr Arg Val Leu His Glu
        355                 360                 365
```

Cys Leu
370

<210> SEQ ID NO 2
<211> LENGTH: 352
<212> TYPE: PRT
<213> ORGANISM: Mus musculus

<400> SEQUENCE: 2

Met Ala Pro Leu Gly Tyr Leu Val Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Ser Thr Gln Pro Ile Leu Cys Ala Ser Ile Pro Gly Leu
            35                  40                  45

Val Pro Lys Gln Leu Arg Phe Cys Arg Asn Tyr Val Glu Ile Met Pro
50                  55                  60

Ser Val Ala Glu Gly Val Lys Ala Gly Ile Gln Glu Cys Gln His Gln
65                  70                  75                  80

Phe Arg Gly Arg Arg Trp Asn Cys Thr Thr Val Ser Asn Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
            115                 120                 125

Ala Glu Gly Ser Ala Ala Ile Cys Gly Cys Ser Ser Arg Leu Gln Gly
        130                 135                 140

Ser Pro Gly Glu Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
210                 215                 220

Arg Thr Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
290                 295                 300

Asp Gly Cys Asp Leu Leu Cys Cys Gly Arg Gly His Asn Ala Arg Thr
305                 310                 315                 320

Glu Arg Arg Arg Glu Lys Cys His Cys Val Phe His Trp Cys Cys Tyr
                325                 330                 335

Val Ser Cys Gln Glu Cys Thr Arg Val Tyr Asp Val His Thr Cys Lys
            340                 345                 350

<210> SEQ ID NO 3

```
<211> LENGTH: 379
<212> TYPE: PRT
<213> ORGANISM: Mus musculus

<400> SEQUENCE: 3

Met Lys Lys Pro Ile Gly Ile Leu Ser Pro Gly Val Ala Leu Gly Thr
1               5                   10                  15

Ala Gly Gly Ala Met Ser Ser Lys Phe Phe Leu Met Ala Leu Ala Thr
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
130                 135                 140

Gly Val Val Asn Ala Met Ser Arg Ala Cys Arg Glu Gly Glu Leu Ser
145                 150                 155                 160

Thr Cys Gly Cys Ser Arg Ala Arg Pro Lys Asp Leu Pro Arg Asp Trp
                165                 170                 175

Leu Trp Gly Gly Cys Gly Asp Asn Ile Asp Tyr Gly His Pro Phe Ala
            180                 185                 190

Lys Glu Phe Val Asp Ala Arg Glu Arg Glu Arg Ile His Ala Lys Gly
        195                 200                 205

Ser Tyr Glu Ser Ala Arg Ile Leu Met Asn Leu His Asn Asn Glu Ala
210                 215                 220

Gly Arg Arg Thr Val Tyr Asn Leu Ala Asp Val Ala Cys Lys Cys His
225                 230                 235                 240

Gly Val Ser Gly Ser Cys Ser Leu Lys Thr Cys Trp Leu Gln Leu Ala
                245                 250                 255

Asp Phe Arg Lys Val Gly Asp Ala Leu Lys Glu Lys Tyr Asp Ser Ala
            260                 265                 270

Ala Ala Met Arg Leu Asn Ser Arg Gly Lys Leu Val Gln Val Asn Ser
        275                 280                 285

Arg Phe Asn Ser Pro Thr Thr Gln Asp Leu Val Tyr Ile Asp Pro Ser
290                 295                 300

Pro Asp Tyr Cys Val Arg Asn Glu Ser Thr Gly Ser Leu Gly Thr Gln
305                 310                 315                 320

Gly Arg Leu Cys Asn Lys Thr Ser Glu Gly Met Asp Gly Cys Glu Leu
                325                 330                 335

Met Cys Cys Gly Arg Gly Tyr Asp Gln Phe Lys Thr Val Gln Thr Glu
            340                 345                 350

Arg Cys His Cys Lys Phe His Trp Cys Cys Tyr Val Lys Cys Lys Lys
        355                 360                 365

Cys Thr Glu Ile Val Asp Gln Phe Val Cys Lys
370                 375

<210> SEQ ID NO 4
```

```
<211> LENGTH: 354
<212> TYPE: PRT
<213> ORGANISM: Mus musculus

<400> SEQUENCE: 4

Met Gly His Leu Leu Met Leu Trp Val Ala Ala Gly Met Cys Tyr Pro
1               5                   10                  15

Ala Leu Gly Ala Ser Ala Trp Ser Val Asn Asn Phe Leu Ile Thr Gly
            20                  25                  30

Pro Lys Ala Tyr Leu Thr Tyr Thr Ala Ser Val Ala Leu Gly Ala Gln
        35                  40                  45

Ile Gly Ile Glu Glu Cys Lys Phe Gln Phe Ala Trp Glu Arg Trp Asn
50                  55                  60

Cys Pro Glu His Ala Phe Gln Phe Ser Thr His Asn Arg Leu Arg Ala
65                  70                  75                  80

Ala Thr Arg Glu Thr Ser Phe Ile His Ala Ile Arg Ser Ala Ala Ile
                85                  90                  95

Met Tyr Ala Val Thr Lys Asn Cys Ser Met Gly Asp Leu Glu Asn Cys
            100                 105                 110

Gly Cys Asp Glu Ser Gln Asn Gly Lys Thr Gly His Gly Trp Ile
        115                 120                 125

Trp Gly Gly Cys Ser Asp Asn Val Glu Phe Gly Glu Lys Ile Ser Arg
130                 135                 140

Leu Phe Val Asp Ser Leu Glu Lys Gly Lys Asp Ala Arg Ala Leu Val
145                 150                 155                 160

Asn Leu His Asn Asn Arg Ala Gly Arg Leu Ala Val Arg Ala Ser Thr
                165                 170                 175

Lys Arg Thr Cys Lys Cys His Gly Ile Ser Gly Ser Cys Ser Ile Gln
            180                 185                 190

Thr Cys Trp Leu Gln Leu Ala Asp Phe Arg Gln Met Gly Asn Tyr Leu
        195                 200                 205

Lys Ala Lys Tyr Asp Arg Ala Leu Lys Ile Glu Met Asp Lys Arg Gln
    210                 215                 220

Leu Arg Ala Gly Asn Arg Ala Glu Gly Arg Trp Ala Leu Thr Glu Ala
225                 230                 235                 240

Phe Leu Pro Ser Thr Glu Ala Glu Leu Ile Phe Leu Glu Gly Ser Pro
                245                 250                 255

Asp Tyr Cys Asn Arg Asn Ala Ser Leu Ser Ile Gln Gly Thr Glu Gly
            260                 265                 270

Arg Glu Cys Leu Gln Asn Ala Arg Ser Ala Ser Arg Glu Gln Arg
        275                 280                 285

Ser Cys Gly Arg Leu Cys Thr Glu Cys Gly Leu Gln Val Glu Glu Arg
290                 295                 300

Arg Ala Glu Ala Val Ser Ser Cys Asp Cys Asn Phe Gln Trp Cys Cys
305                 310                 315                 320

Thr Val Lys Cys Gly Gln Cys Arg Arg Val Val Ser Arg Tyr Tyr Cys
                325                 330                 335

Thr Arg Pro Val Gly Ser Ala Arg Pro Arg Gly Arg Gly Lys Asp Ser
            340                 345                 350

Ala Trp

<210> SEQ ID NO 5
<211> LENGTH: 352
<212> TYPE: PRT
<213> ORGANISM: Homo sapiens
```

<400> SEQUENCE: 5

| | | | | | | | | | | | | | | |
|---|---|---|---|---|---|---|---|---|---|---|---|---|---|---|
|Met|Ala|Pro|Leu|Gly|Tyr|Phe|Leu|Leu|Leu|Cys|Ser|Leu|Lys|Gln|Ala|
|1| | | |5| | | | |10| | | | |15|
|Leu|Gly|Ser|Tyr|Pro|Ile|Trp|Trp|Ser|Leu|Ala|Val|Gly|Pro|Gln|Tyr|
| | | | |20| | | | |25| | | | |30| |
|Ser|Ser|Leu|Gly|Ser|Gln|Pro|Ile|Leu|Cys|Ala|Ser|Ile|Pro|Gly|Leu|
| | | | |35| | | | |40| | | | |45| |
|Val|Pro|Lys|Gln|Leu|Arg|Phe|Cys|Arg|Asn|Tyr|Val|Glu|Ile|Met|Pro|
| |50| | | | |55| | | | |60| | | | |
|Ser|Val|Ala|Glu|Gly|Ile|Lys|Ile|Gly|Ile|Gln|Glu|Cys|Gln|His|Gln|
|65| | | | |70| | | | |75| | | | |80|
|Phe|Arg|Gly|Arg|Arg|Trp|Asn|Cys|Thr|Thr|Val|His|Asp|Ser|Leu|Ala|
| | | | |85| | | | |90| | | | |95| |
|Ile|Phe|Gly|Pro|Val|Leu|Asp|Lys|Ala|Thr|Arg|Glu|Ser|Ala|Phe|Val|
| | | |100| | | | |105| | | | |110| | |
|His|Ala|Ile|Ala|Ser|Ala|Gly|Val|Ala|Phe|Ala|Val|Thr|Arg|Ser|Cys|
| | | |115| | | | |120| | | | |125| | |
|Ala|Glu|Gly|Thr|Ala|Ala|Ile|Cys|Gly|Cys|Ser|Ser|Arg|His|Gln|Gly|
| |130| | | | |135| | | | |140| | | | |
|Ser|Pro|Gly|Lys|Gly|Trp|Lys|Trp|Gly|Gly|Cys|Ser|Glu|Asp|Ile|Glu|
|145| | | | |150| | | | |155| | | | |160|
|Phe|Gly|Gly|Met|Val|Ser|Arg|Glu|Phe|Ala|Asp|Ala|Arg|Glu|Asn|Arg|
| | | | |165| | | | |170| | | | |175| |
|Pro|Asp|Ala|Arg|Ser|Ala|Met|Asn|Arg|His|Asn|Asn|Glu|Ala|Gly|Arg|
| | | |180| | | | |185| | | | |190| | |
|Gln|Ala|Ile|Ala|Ser|His|Met|His|Leu|Lys|Cys|Lys|Cys|His|Gly|Leu|
| | | |195| | | | |200| | | | |205| | |
|Ser|Gly|Ser|Cys|Glu|Val|Lys|Thr|Cys|Trp|Trp|Ser|Gln|Pro|Asp|Phe|
|210| | | | |215| | | | |220| | | | | |
|Arg|Ala|Ile|Gly|Asp|Phe|Leu|Lys|Asp|Lys|Tyr|Asp|Ser|Ala|Ser|Glu|
|225| | | | |230| | | | |235| | | | |240|
|Met|Val|Val|Glu|Lys|His|Arg|Glu|Ser|Arg|Gly|Trp|Val|Glu|Thr|Leu|
| | | | |245| | | | |250| | | | |255| |
|Arg|Pro|Arg|Tyr|Thr|Tyr|Phe|Lys|Val|Pro|Thr|Glu|Arg|Asp|Leu|Val|
| | | |260| | | | |265| | | | |270| | |
|Tyr|Tyr|Glu|Ala|Ser|Pro|Asn|Phe|Cys|Glu|Pro|Asn|Pro|Glu|Thr|Gly|
| | | |275| | | | |280| | | | |285| | |
|Ser|Phe|Gly|Thr|Arg|Asp|Arg|Thr|Cys|Asn|Val|Ser|Ser|His|Gly|Ile|
| |290| | | | |295| | | | |300| | | | |
|Asp|Gly|Cys|Asp|Leu|Leu|Cys|Cys|Gly|Arg|Gly|His|Asn|Ala|Arg|Ala|
|305| | | | |310| | | | |315| | | | |320|
|Glu|Arg|Arg|Arg|Glu|Lys|Cys|Arg|Cys|Val|Phe|His|Trp|Cys|Cys|Tyr|
| | | | |325| | | | |330| | | | |335| |
|Val|Ser|Cys|Gln|Glu|Cys|Thr|Arg|Val|Tyr|Asp|Val|His|Thr|Cys|Lys|
| | | |340| | | | |345| | | | |350| | |

<210> SEQ ID NO 6
<211> LENGTH: 355
<212> TYPE: PRT
<213> ORGANISM: Homo sapiens

<400> SEQUENCE: 6

| | | | | | | | | | | | | | | |
|---|---|---|---|---|---|---|---|---|---|---|---|---|---|---|
|Met|Gly|Asn|Leu|Phe|Met|Leu|Trp|Ala|Ala|Leu|Gly|Ile|Cys|Cys|Ala|
|1| | | |5| | | | |10| | | | |15|
|Ala|Phe|Ser|Ala|Ser|Ala|Trp|Ser|Val|Asn|Asn|Phe|Leu|Ile|Thr|Gly|

```
                     20                  25                  30
Pro Lys Ala Tyr Leu Thr Tyr Thr Ser Val Ala Leu Gly Ala Gln
             35                  40                  45
Ser Gly Ile Glu Glu Cys Lys Phe Gln Phe Ala Trp Glu Arg Trp Asn
 50                  55                  60
Cys Pro Glu Asn Ala Leu Gln Leu Ser Thr His Asn Arg Leu Arg Ser
 65                  70                  75                  80
Ala Thr Arg Glu Thr Ser Phe Ile His Ala Ile Ser Ser Ala Gly Val
                 85                  90                  95
Met Tyr Ile Ile Thr Lys Asn Cys Ser Met Gly Asp Phe Glu Asn Cys
                100                 105                 110
Gly Cys Asp Gly Ser Asn Asn Gly Lys Thr Gly His Gly Trp Ile
            115                 120                 125
Trp Gly Gly Cys Ser Asp Asn Val Glu Phe Gly Glu Arg Ile Ser Lys
            130                 135                 140
Leu Phe Val Asp Ser Leu Glu Lys Gly Lys Asp Ala Arg Ala Leu Met
145                 150                 155                 160
Asn Leu His Asn Asn Arg Ala Gly Arg Leu Ala Val Arg Ala Thr Met
                165                 170                 175
Lys Arg Thr Cys Lys Cys His Gly Ile Ser Gly Ser Cys Ser Ile Gln
            180                 185                 190
Thr Cys Trp Leu Gln Leu Ala Glu Phe Arg Glu Met Gly Asp Tyr Leu
            195                 200                 205
Lys Ala Lys Tyr Asp Gln Ala Leu Lys Ile Glu Met Asp Lys Arg Gln
            210                 215                 220
Leu Arg Ala Gly Asn Ser Ala Glu Gly His Trp Val Pro Ala Glu Ala
225                 230                 235                 240
Phe Leu Pro Ser Ala Glu Ala Glu Leu Ile Phe Leu Glu Glu Ser Pro
                245                 250                 255
Asp Tyr Cys Thr Cys Asn Ser Ser Leu Gly Ile Tyr Gly Thr Glu Gly
            260                 265                 270
Arg Glu Cys Leu Gln Asn Ser His Asn Thr Ser Arg Trp Glu Arg Arg
            275                 280                 285
Ser Cys Gly Arg Leu Cys Thr Glu Cys Gly Leu Gln Val Glu Glu Arg
            290                 295                 300
Lys Thr Glu Val Ile Ser Ser Cys Asn Cys Lys Phe Gln Trp Cys Cys
305                 310                 315                 320
Thr Val Lys Cys Asp Gln Cys Arg His Val Val Ser Lys Tyr Tyr Cys
                325                 330                 335
Ala Arg Ser Pro Gly Ser Ala Gln Ser Leu Gly Arg Val Trp Phe Gly
            340                 345                 350
Val Tyr Ile
    355

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caacagtagc aaggagcatg gactgttg                                     28

<210> SEQ ID NO 8
```

-continued

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ggctgggtcc aggtcgttta					20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gacaaaccgg gagtcagcct ttgtc					25

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tgctgcaccc acagatagca					20

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gtacatgcgc tctgctgcca tcatgtac					28

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gactcgtcac agccgcagtt					20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
acggaagccc aagaacctga					20

<210> SEQ ID NO 14
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 14
cattgctgga gttaccgctg                                                   20

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
taaatctaag acgccagcag gtcctgctg                                         29

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgacccagcc aaagaccct                                                    19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccatccgtct cggctttgt                                                    19

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
cggataaaaa agagctgtgc gcgc                                              24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccaggcagac aagttctctc ct                                                22

<210> SEQ ID NO 20
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 20
cttgtagtca atgttgccgg c                                            21

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
caactgtttg cgctgacacc catgga                                       26

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcagagaggt tctccaaaga gg                                           22

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagattgccg gtaacgtcag g                                            21

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
atcgaccaga tgttcgcagc ctttcc                                       26

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgcaccacca actgcttag                                               19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 26
ggatgcaggg atgatgttc                                                19

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cagaagactg tggatggccc ctc                                           23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaggtgaaga cctgctggtg ggc                                           23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttgggctca caaaagttgg                                               20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcctgaccct gaagtacccc                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtggtggtga agctgtagcc                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
```

```
gccctgacca ctccagttta                                              20
```

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
ggagtcctgg atttccttcc                                              20
```

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
gaaccagagg ggagagacag a                                            21
```

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
ccctcagctt gcttttagg ag                                            22
```

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

```
gaggagaatg gccagcagga a                                            21
```

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
gcgaacatct gctccacctc a                                            21
```

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
aggaggcctt cactatcatg g                                            21
```

```
<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtgatgatgt gcaccaggtt c                                              21

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Phospho-serine

<400> SEQUENCE: 40

Gly Lys Glu Ala Pro Pro Ala Pro Pro Gln Ser Pro
1               5                   10
```